US009575050B2

(12) United States Patent
Vrane et al.

(10) Patent No.: US 9,575,050 B2
(45) Date of Patent: Feb. 21, 2017

(54) SLIDER TAPE SEALING CARTRIDGE FOR ADJUSTABLY SEALING A FLOW CYTOMETER SAMPLE MANIPULATION CHAMBER

(71) Applicant: Becton, Dickinson and Company, Franklin Lakes, NJ (US)

(72) Inventors: David Vrane, San Jose, CA (US); Pierce O. Norton, Los Gatos, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 10 days.

(21) Appl. No.: 14/686,367

(22) Filed: Apr. 14, 2015

(65) Prior Publication Data

US 2015/0301014 A1    Oct. 22, 2015

Related U.S. Application Data

(60) Provisional application No. 61/982,164, filed on Apr. 21, 2014.

(51) Int. Cl.
*G01N 33/483* (2006.01)
*B01L 99/00* (2010.01)

(52) U.S. Cl.
CPC ................ *G01N 33/4833* (2013.01)

(58) Field of Classification Search
CPC ............ G01N 15/12; G01N 2015/1081; G01N 15/1218; G01N 15/14; G01N 2015/149
See application file for complete search history.

(56) References Cited

U.S. PATENT DOCUMENTS

| 2,606,652 | A | 8/1952 | Jaquette et al. |
| 4,162,024 | A | 7/1979 | Shanley |
| 5,441,708 | A | 8/1995 | Diccianni et al. |
| 5,641,457 | A | 6/1997 | Vardanega et al. |
| 5,700,692 | A | 12/1997 | Sweet |
| 5,776,781 | A | 7/1998 | Vardanega et al. |
| 6,014,904 | A | 1/2000 | Lock |
| 6,372,506 | B1 | 4/2002 | Norton |
| 6,510,007 | B1 | 1/2003 | Blasenheim |
| 6,683,314 | B2 | 1/2004 | Oostman, Jr. et al. |
| 6,809,804 | B1 | 10/2004 | Yount et al. |
| 6,880,414 | B2 | 4/2005 | Norton |
| 6,944,338 | B2 | 9/2005 | Lock et al. |
| 7,129,505 | B2 | 10/2006 | Oostman, Jr. et al. |
| 7,201,875 | B2 | 4/2007 | Norton et al. |
| 7,544,326 | B2 | 6/2009 | Norton et al. |
| 2002/0042148 | A1 | 4/2002 | Monard |

(Continued)

FOREIGN PATENT DOCUMENTS

WO    01/85088 A1    11/2001

OTHER PUBLICATIONS

BD Biosciences, BD FACSDiva Software Quick Reference Guide for BD FACSAria Cell Sorters, Jan. 2009, 8 pages, Available online: http://www.bdbiosciences.com/documents/facsdivav61_aria_quickrefguide.pdf.

(Continued)

*Primary Examiner* — Paul Hyun
(74) *Attorney, Agent, or Firm* — Kyle A. Gurley; Bret E. Field; Bozicevic, Field & Francis LLP

(57) ABSTRACT

Flow cytometer systems that include a sample manipulation chamber having an access hole that is adjustably sealed by a slider tape sealing cartridge are provided. Also provided are methods of using such systems, as well as components for use in such systems.

20 Claims, 11 Drawing Sheets

(56) References Cited

U.S. PATENT DOCUMENTS

2012/0024857 A1    2/2012    Kodama et al.
2013/0309763 A1    11/2013    Hashimoto et al.

OTHER PUBLICATIONS

BD Biosciences, BD FACSAria III User's Guide, May 2012, 346 pages, Available online: http://www.bdbiosciences.com/documents/BD_FACSAria_III_User_Guide.pdf.
BD Biosciences, BD FACSAria III Cell Sorter: Technical Specifications, 2010, 4 pages, Available online: http://www.bdbiosciences.com/documents/BD_FACSAria_III_tech_specs.pdf.
BD Biosciences, BD FACSAria III Cell Sorter Brochure, 2010, 16 pages, Available online: http://www.bdbiosciences.com/documents/BD_FACSAria_III_brochure.pdf.
BD Biosciences, BD FACSAria Fusion Cell Sorter: Technical Specifications, 23-15075-02, label approval notification Jul. 16, 2014, available in print Aug. 11, 2014, 4 pages, Available online: http://www.bdbiosciences.com/documents/BD_FACSAria_fusion_tech_specs.pdf.
BD Biosciences, BD FACSAria Fusion Cell Sorter: Recommended Filter Guide, 23-15074-0, label approval notification Sep. 25, 2014, available in print Oct. 6, 2014, 1 page, Available online: http://www.bdbiosciences.com/documents/BD_FACSAria_fusion_filter_guide.pdf.
BD Biosciences, BD FACSAria Fusion Brochure, 23-14994-0, label approval notification Aug. 7, 2014, available in print Sep. 4, 2014, 20 pages, Available online: http://www.bdbiosciences.com/documents/BD_FACSAria_fusion_brochure.pdf.

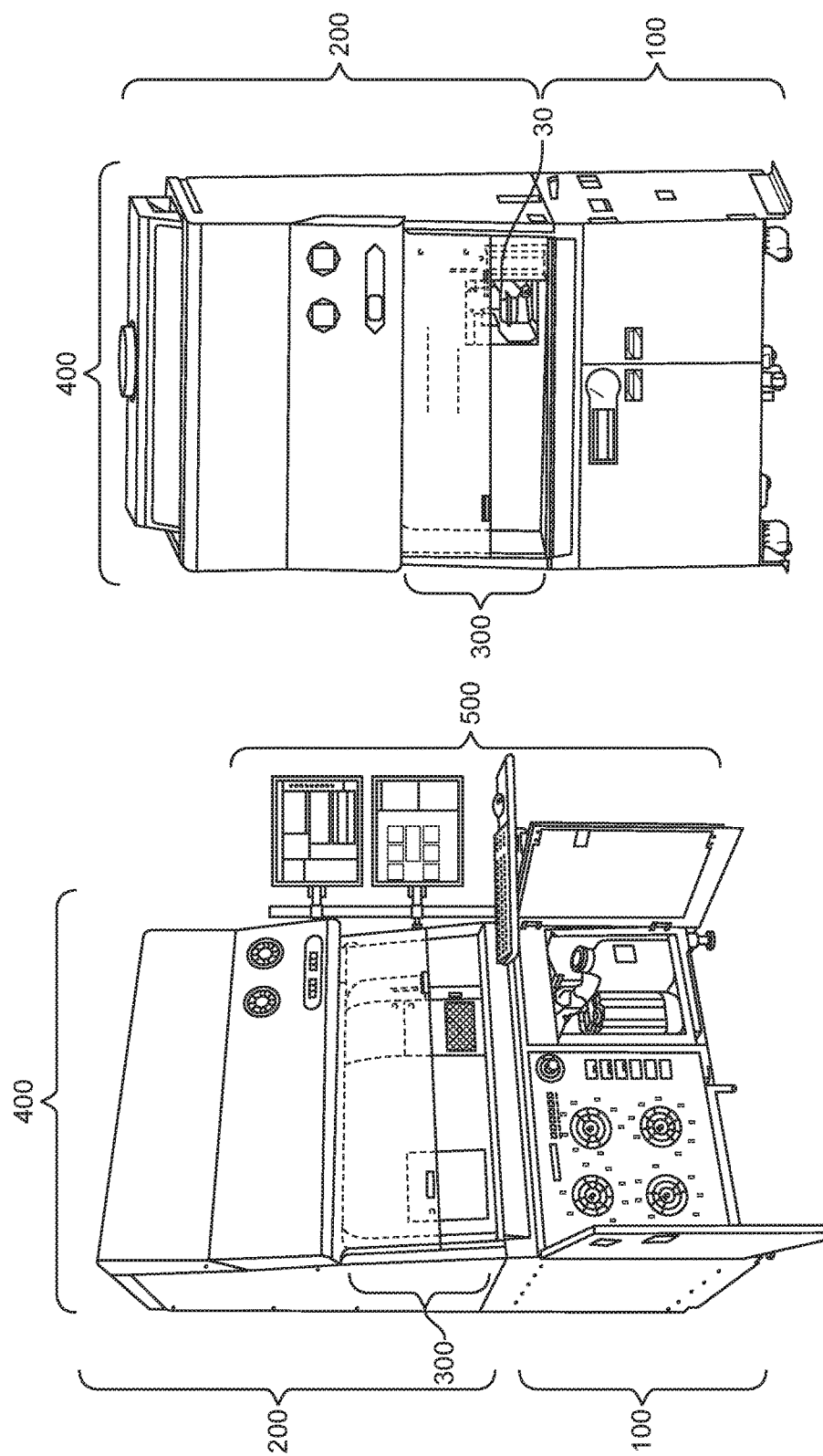

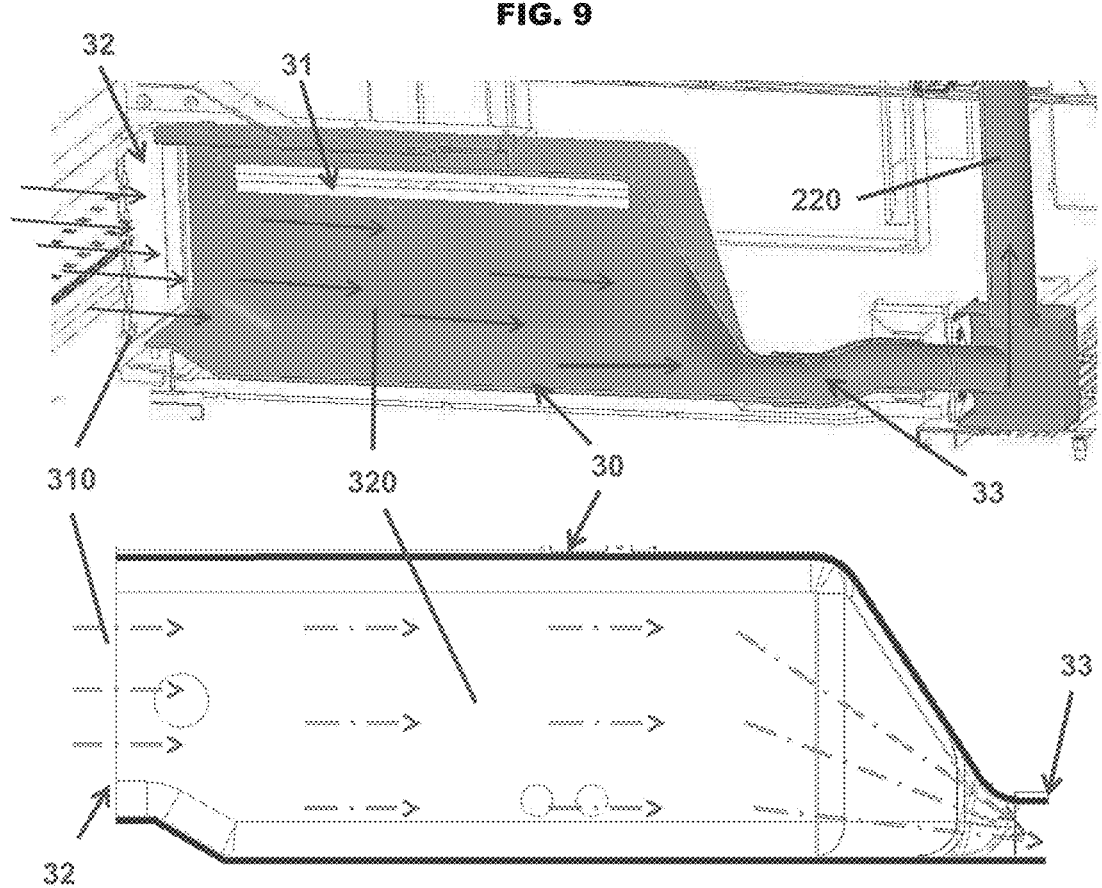

SLIDER TAPE SEALING CARTRIDGE FOR ADJUSTABLY SEALING A FLOW CYTOMETER SAMPLE MANIPULATION CHAMBER

CROSS-REFERENCE TO RELATED APPLICATIONS

Pursuant to 35 U.S.C. §119 (e), this application claims priority to the filing date of U.S. Provisional Patent Application Ser. No. 61/982,164 filed Apr. 21, 2014, the disclosure of which application is herein incorporated by reference.

INTRODUCTION

Flow cytometers are valuable laboratory instruments for the analysis and isolation of biological particles, such as cells and constituent molecules. Flow cytometers utilize a fluid stream to linearly segregate particles such that they can pass, single file, through a detection apparatus measuring properties such as light scattering and/or fluorescence. Individual cells can then be characterized according to the measured properties (light scattering, the presence of detectable markers, etc.). Thus, flow cytometers can be used, for example, to produce a profile (e.g., a diagnostic profile) of a population of biological particles. Some flow cytometers can be used to sort the biological particles based on their measured properties.

SUMMARY

Flow cytometer systems that include a sample manipulation chamber having an access hole that is adjustably sealed by a slider tape sealing cartridge are provided. Also provided are methods of using such systems, and well as components for use in such systems.

Flow cytometric analysis of a biological sample can generate aerosols, usually in regions where particles are analyzed, sorted, and/or collected. There is a need to allow the manipulation of samples (e.g., by a mobile arm, e.g., an automated robotic arm) during sorting, and/or collection while providing biosafety containment of flow cytometer instruments (e.g., cell sorters) that are used to process hazardous substances such as hazardous chemicals and/or toxic or infectious particles. In some cases, the removal of aerosols relies on air flow, but the flow of air across regions where particles are analyzed, sorted, and/or collected (e.g., within a sample manipulation chamber) can result in cross-sample contamination. Cross-sample contamination can be exacerbated by the presence of an unsealed access hole (e.g., to allow penetration into the sample manipulation chamber by a mobile arm) in the sample manipulation chamber.

Components are provided that mitigate aerosols generated during operation of a flow cytometer while reducing air flow disturbances within a sample manipulation chamber that would otherwise cause cross-sample contamination. In some cases, a flow cytometer includes a mobile arm that penetrates into a sample manipulation chamber to manipulate samples. In some such cases, an access hole of the sample manipulation chamber is adjustably sealed with a sealing cartridge that can maintain a seal while preserving mobility of the mobile arm. In some embodiments, a flow cytometer system includes a biosafety hood designed to enclose an integrated flow cytometer. A flow cytometer system can include various combinations of: a flow cytometer instrument base, a flow cytometer, and a biosafety hood (BSH). In some cases, a BSH includes an aerosol management system (AMS), which provides a redundant air filtration system. In some cases, the AMS is fluidically coupled to an adjustably sealed sample manipulation chamber.

Provided components include a flow cytometer, a sample manipulation chamber with an attached sealing cartridge, a sealing cartridge, and a slider tape. It can be desirable to reduce the footprint of a subject sealing cartridge. For example, in some cases, a subject sealing cartridge is attached to (and adjustably seals) a sample manipulation chamber that is associated with a larger instrument (e.g., a flow cytometer). In some such cases, the dimensions of the larger instrument can place space constraints on the dimensions of the sample manipulation chamber and/or the sealing cartridge. The provided slider tape and sealing cartridge have a small footprint that can alleviate space constraints. Also provided are methods, including methods of performing a flow cytometric procedure using the components above.

BRIEF DESCRIPTION OF THE FIGURES

FIG. 5A-5B depict one embodiment of a flow cytometer system 400 that includes a flow cytometer instrument base 100, a biosafety hood (BSH) 200, a flow cytometer 300, where the flow cytometer 300 includes a sample manipulation chamber 30.

FIG. 7A depicts a step of introducing a sample into a sample loading region 310 of a flow cytometer 300 of a subject flow cytometer system that includes a flow cytometer instrument base 100, and biosafety hood (BSH) 200. FIG. 7B depicts an operator (i.e., a user) manipulating a sample within a particle collection region 330 of a flow cytometer 300, where the particle collection region 330 has an enclosing sample manipulation chamber 30, and where the flow cytometer system includes a BSH. FIG. 7C depicts a flow cytometer instrument base 100 that houses spectral filters and detector arrays of an associated flow cytometer. FIG. 7D depicts a flow cytometer instrument base 100 having multiple removable fluid sources in a drawer that is extendible from the base.

FIG. 9 (a zoom of FIG. 8A-8B) depicts cutaway schematics of one embodiment of a flow cytometer system where the efflux opening 33 of a sample manipulation chamber 30 of a particle collection region 320 of a flow cytometer is fluidically coupled via conduit 220 to an aerosol management system (AMS) of a biosafety hood (BSH). The particle collection region 320 has an air filter 310 covering an influx opening 32 (of the sample manipulation chamber 30), which is facing toward the front of the flow cytometer. When the AMS is operating, air flows (depicted with arrows) from the front of the flow cytometer, through the forward-facing air filter 310, through the influx opening 32 of the sample manipulation chamber 30 of the particle collection region 320, toward the back of the flow cytometer, out the efflux opening 33 of the sample manipulation chamber 30, into the conduit 220 and toward the AMS.

DETAILED DESCRIPTION

Figure 1A:
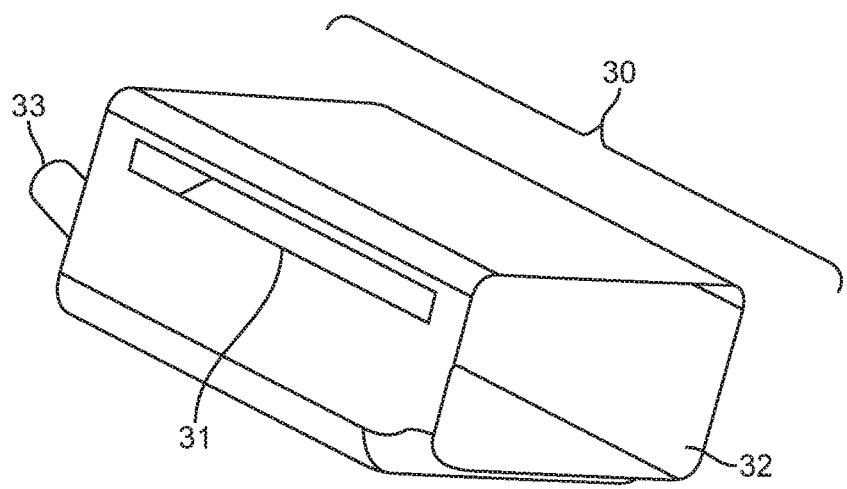
FIG. 1A-1D depict one embodiment of a sample manipulation chamber 30 that includes an influx opening 32, an efflux opening 33, and an access hole 31. Also depicted are components (41 and 42) of a flow cytometer that are operably coupled to the sample manipulation chamber 30. Simulated airflow streamlines 38, caused by simulated air flow through a sample manipulation chamber 30 with a closed or open access hole 31, are depicted in FIG. 1C and FIG. 1D.

Flow cytometer systems that include a sample manipulation chamber having an access hole that is adjustably sealed by a slider tape sealing cartridge are provided. Also provided are methods of using such systems, and well as components for use in such systems.

Flow cytometers, flow cytometer systems, and flow cytometer components are provided that mitigate aerosols generated during operation of a flow cytometer while reducing air flow disturbances within a sample manipulation chamber that would otherwise cause cross-sample contamination. In some cases, a flow cytometer includes a mobile arm that penetrates into a sample manipulation chamber to manipulate samples. In some such cases, an access hole of the sample manipulation chamber is adjustably sealed with a sealing cartridge that can maintain a seal while preserving mobility of the mobile arm. In some embodiments, a flow cytometer system includes a biosafety hood designed to enclose an integrated flow cytometer. A flow cytometer system can include various combinations of: a flow cytometer instrument base, a flow cytometer, and a biosafety hood (BSH). In some cases, a BSH includes an aerosol management system (AMS), which provides a redundant air filtration system. In some cases, the AMS is fluidically coupled to an adjustably sealed sample manipulation chamber.

Provided components include a flow cytometer, a sample manipulation chamber with an attached sealing cartridge, a sealing cartridge, and a slider tape. It can be desirable to reduce the footprint of a subject sealing cartridge. For example, in some cases, a subject sealing cartridge is attached to (and adjustably seals) a sample manipulation chamber that is associated with a larger instrument (e.g., a flow cytometer). In some such cases, the dimensions of the larger instrument can place space constraints on the dimensions of the sample manipulation chamber and/or the sealing cartridge. The provided slider tape and sealing cartridge have a small footprint that can alleviate space constraints. Also provided are methods, including methods of performing a flow cytometric procedure using the components above.

Before embodiments of the present disclosure are described in greater detail, it is to be understood that this disclosure is not limited to particular embodiments described, as such may, of course, vary. The disclosure encompasses various alternatives, modifications, and equivalents, as will be appreciated by those of skill in the art. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present disclosure. Any recited method can be carried out in the order of events recited or in any other order which is logically possible.

Any publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates which may need to be independently confirmed.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, representative illustrative methods and materials are now described.

In further describing embodiments of the present disclosure, aspects of embodiments of the flow cytometer systems will be described in greater detail. Methods of using the subject flow cytometer systems will then be reviewed.

Flow Cytometer and Flow Cytometer System

Figure 6B:
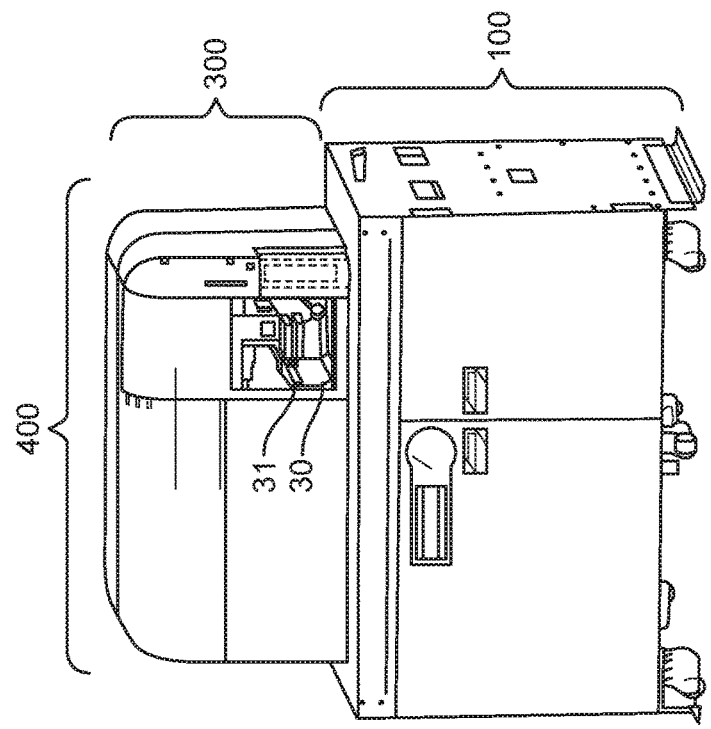
FIG. 6A-6B depict one embodiment of a flow cytometer system 400 that includes a flow cytometer instrument base 100, and a flow cytometer 300, where the flow cytometer 300 includes a sample manipulation chamber 30.

Aspects of the disclosure include flow cytometer systems and flow cytometers. Aspects of the disclosure also include individual components of a flow cytometer and/or flow cytometer system (e.g., a flow cytometer, a flow cytomoter that includes a mobile arm, a sample manipulation chamber, a sealing cartridge, a slider tape, etc.). A flow cytometer system can include various combinations of the following components: a flow cytometer, a flow cytometer instrument base, and a biosafety hood (BSH). In some embodiments, a subject flow cytometer system includes a flow cytometer instrument base, a flow cytometer, and a BSH (FIG. 5). In some embodiments, a subject flow cytometer system includes a flow cytometer instrument base and a flow cytometer (FIG. 6), which components may be integrated. In some cases, a BSH includes an aerosol management system (AMS) operatively coupled to the flow cytometer (e.g., via fluidically coupling with a sample manipulation chamber).

The components of the flow cytometer and/or flow cytometer system, which will now be described in greater detail below, can be made of any convenient durable, rigid material, or combination of materials, including but not limited to: metal (e.g., stainless steel); plastic (e.g., polycarbonate, LEXAN, etc.); and the like. A slider tape (e.g., of a sealing cartridge) can be made of any convenient material that allows the slider tape to reversibly wind upon itself (see e.g., FIG. 2 and FIG. 3). In some cases, the slider tape includes polytetrafluoroethylene (PTFE).

Slider Tape

A subject slider tape includes a flexible member having a first end and a second end, where the first end of the slider tape can reversibly wind upon itself (i.e., is reversibly windable). A slider tape also includes an access hole positioned in the elongated flexible member between the first and second ends. In addition, a slider tape is configured to slide within a track and adjustably seal an opening of a sample manipulation chamber.

Flexible Member

Figure 3:
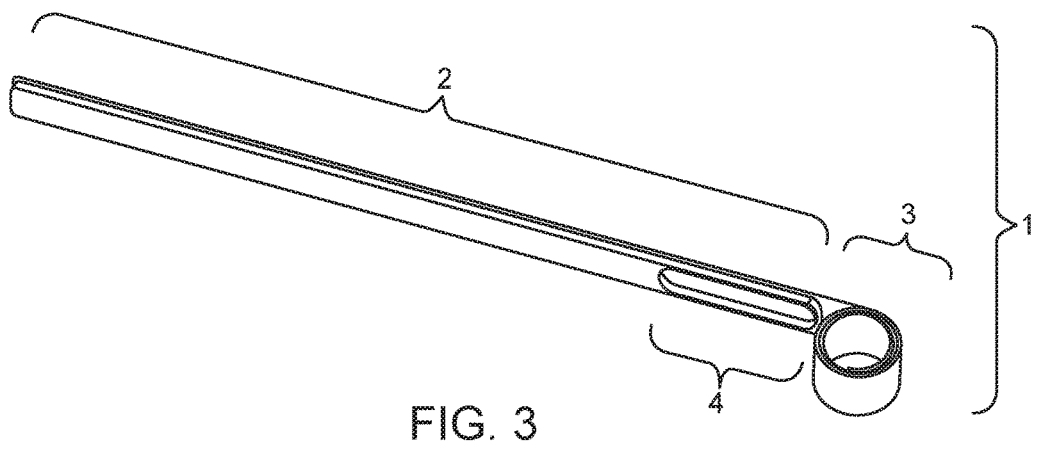
FIG. 3 depicts one embodiment of a slider tape 1 that is configured to slide within a track and adjustably seal an opening (i.e., access hole) of a sample manipulation chamber 30. The depicted slider tap 1 can reversibly wind upon itself at one end 3 and has a rigid region 2 that extends from one end of the slider tape 1 to surround the access hole 4 of the slider tape 1.

The slider tape is a flexible member with an end that can wind upon itself (FIG. 3). In some cases, both first and second ends of the flexible member can wind upon themselves. In some cases, the slider tape is elongated such that there exists two clear "ends." However, in some cases, the elongation of the slider tape is not as exaggerated or an elongation is not at all present (e.g., the slider tape can be a square). Thus, in some cases, it is possible to have multiple ends that can wind upon themselves (e.g., a square or rectangular slider tape can have up to 4 ends, a pentagonal slider tape can have up to 5 ends, etc.). The size and shape of slider tape can be any convenient size and shape, and can depend on multiple factors (e.g., the size and shape of an access hole of a chamber which the slider tape is intended to adjustably seal, the size and shape of a casing that will form a sealing cartridge with the slider tape, the size and shape of an access hole of an associated casing, the size and shape of a track along which the slider tape with move, the size and shape of an associated winder, etc.). In some cases, the shape of a slider tape is selected from: a square, a rectangle, a rectangle with rounded corners, a pentagon, a hexagon, a polygon, an elipse, a triangle, a trapezoid, a rhomboid, and a circle.

The exact dimensions and shape of a slider tape will depend on the intended purpose of the slider tape. For example, the length of a slider tape can be any convenient length. In some embodiments (e.g., when a slider tape is intended to adjustably seal a sample manipulation chamber of a flow cytometer), the length of a slider tape can be in a range of from 2 inches to 30 inches (e.g., from 2 inches to 25 inches, from 2 inches to 20 inches, from 4 inches to 18 inches, from 5 inches to 17 inches, from 6 inches to 16 inches, from 7 inches to 15 inches, from 8 inches to 14 inches, from 9 inches to 13 inches, from 10 inches to 12 inches, from 5 inches to 25 inches, from 10 inches to 25 inches, or from 10 inches to 20 inches).

The width of a slider tape can be any convenient width. In some embodiments (e.g., when a slider tape is intended to adjustably seal a sample manipulation chamber of a flow cytometer), the width of a slider tape can be in a range of from 0.1 inches to 4.5 inches (e.g., from 0.1 inches to 3.5 inches, from 0.1 inches to 2.5 inches, from 0.1 inches to 1.5 inches, from 0.3 inches to 1.2 inches, from 0.5 inches to 1 inch, from 0.6 inches to 0.9 inches, or from 0.7 inches to 0.9 inches).

The thickness of a slider tape slider tape (e.g., a reversibly windable region, a rigid region as discussed below, etc.) can be any convenient thickness, and can depend on the material with which the slider tape is made. In some embodiments (e.g., when a slider tape is intended to adjustably seal a sample manipulation chamber of a flow cytometer), the thickness of a slider tape (e.g., a reversibly windable region, a rigid region as discussed below, etc.) can be in a range of from 0.005 inches to 1 inch (e.g., from 0.01 inches to 0.1 inches, from 0.02 inches to 0.2 inches, from 0.03 inches to 0.3 inches, from 0.04 inches to 0.4 inches, from 0.05 inches to 0.5 inches, from 0.08 inches to 0.8 inches, from 0.09 inches to 0.9 inches, from 0.1 inches to 0.8 inches, from 0.005 inches to 0.1 inches, from 0.008 inches to 0.08 inches, from 0.009 inches to 0.05 inches, from 0.01 inches to 0.04 inches, from 0.01 inches to 0.03 inches, from 0.05 inches to 0.8 inches, from 0.05 inches to 0.3 inches, from 0.05 inches to 0.2 inches, from 0.08 inches to 0.2 inches, from 0.09 inches to 0.18 inches, from 0.09 inches to 0.15 inches, from 0.1 inches to 0.15 inches, from 0.11 inches to 0.14 inches, or from 0.12 inches to 0.13 inches).

An exemplary slider tape that is intended to adjustably seal a sample manipulation chamber of a flow cytometer is 10 to 12 inches long, 0.7 to 0.9 inches wide, 0.125 inches thick in a rigid region (discussed below) and 0.02 inches thick in a region (e.g., and at end) that can reversibly wind upon itself.

The material composition of the slider tape can include any convenient material. In some case, the material composition of the slider tape includes polytetrafluoroethylene (PTFE). In some cases, the material composition of the slider tape is 100% PTFE. In some cases, the material composition of the slider tape is 50% or more PTFE (e.g., 50% or more, 60% or more, 70% or more, 80% or more, 90% or more, 95% or more, 98% or more, or 99% or more). In some cases, the PTFE is plasticized.

Slider Tape Access Hole

A subject slider tape includes an access hole (e.g., at least one access hole, one access hole, up to 2 access holes, up to 3 access holes, up to 4 access holes, etc.). The exact dimensions and shape of an access hole of a slider tape will depend on various factors, including, for example, the size and shape of a mobile arm that is intended to penetrate the access hole, the size and shape of the slider tape, etc.

The shape of an access hole of the sample manipulation chamber can be any convenient shape. For example, in some cases, the shape of an access hole of the sample manipulation chamber is selected from: a square, a rectangle, a rectangle with rounded corners, a pentagon, a hexagon, a polygon, an ellipse, a triangle, a trapezoid, a rhomboid, and a circle.

The area of a slider tape access hole can be any convenient area. In some embodiments (e.g., when a slider tape is intended to adjustably seal a sample manipulation chamber of a flow cytometer), the area of a slider tape access hole can be in a range of from 0.2 square inches to 5 square inches (e.g., from 0.2 square inches to 4.5 square inches, from 0.2 square inches to 4 square inches, from 0.2 square inches to 3.5 square inches, from 0.2 square inches to 3 square inches, from 0.2 square inches to 2.5 square inches, from 0.2 square inches to 2 square inches, from 0.2 square inches to 1.5 square inches, from 0.2 square inches to 1 square inch).

Rigid Region

In some embodiments, a slider tape includes a rigid region. A rigid region is a region of the slider tape that cannot wind upon itself (i.e., a region that is not reversibly windable). For example, see region 2 of FIG. 3. The rigidity of the rigid region can be conferred by any convenient character. For example, in some cases the rigid region can be made of a material that contributes to rigidity. For example, in some cases, the rigid region includes an acrylic-polyvinyl chloride composite (e.g., KYDEX). In some cases, a character of the rigid region that contributes to rigidity is thickness. Thus, in some cases, the rigid region of a slider tape is thicker than a region that can reversibly wind upon itself (e.g., one of the ends). In some cases, the rigid region can be 1.2-fold or more thicker (e.g., 1.4-fold or more, 1.6-fold or more, 1.8-fold or more, 2-fold or more, 2.5-fold or more, 3-fold or more, 3.5-fold or more, 4-fold or more, 4.5-fold or more, 5-fold or more, 5.5-fold or more, 6-fold or more, 6.5-fold or more, 7-fold or more, 7.5-fold or more, 8-fold or more, 9-fold or more, 10-fold or more, etc.) than a region that can reversibly wind upon itself (e.g., a reversibly windable end of the slider tape).

The rigid region of a slider tape can be any convenient thickness (e.g., a rigid region can be thicker than a reversibly windable region), and the thickness can depend on the intended purpose of the slider tape. In some cases (e.g., when a slider tape is intended to adjustably seal a sample manipulation chamber of a flow cytometer), the thickness of a rigid region of a slider tape can be in a range of from 0.005 inches to 1 inch (e.g., from 0.01 inches to 0.1 inches, from 0.02 inches to 0.2 inches, from 0.03 inches to 0.3 inches, from 0.04 inches to 0.4 inches, from 0.05 inches to 0.5 inches, from 0.08 inches to 0.8 inches, from 0.09 inches to 0.9 inches, from 0.1 inches to 0.8 inches, from 0.05 inches to 0.8 inches, from 0.05 inches to 0.3 inches, from 0.05 inches to 0.2 inches, from 0.08 inches to 0.2 inches, from 0.09 inches to 0.18 inches, from 0.09 inches to 0.15 inches, from 0.1 inches to 0.15 inches, from 0.11 inches to 0.14 inches, or from 0.12 inches to 0.13 inches).

In some cases, the rigid region surrounds an access hole of the slider tape (FIG. 3). In some cases, the rigid region surrounds an access hole of the slider tape, but does not extend to an end of the slider tape. For example, in cases where two ends of the slider tape can reversibly wind upon themselves, neither of the two ends would be considered to be part of the rigid region. In some cases, a rigid region extends from an end of the slider tape and surrounds an access hole of the slider tape (FIG. 3).

Sealing Cartridge

A sealing cartridge includes a slider tape and a winder. A winder is a region in which the slider tape reversibly winds upon itself as more and more of the slider tape enters the winder. For example a winder can be a cylinder (i.e., a cylindrical canister) (see, e.g., FIG. 2 and FIG. 4). In some cases, a sealing cartridge includes two winders. For example, if both ends of an elongated slider tape can wind upon themselves, then a winder at either end will allow each end to wind upon itself as more and more of the slider tape enders the winder. In some cases, as discusses above, a slider tape has more than two ends that can reversibly wind upon themselves. Thus, in some cases, a sealing cartridge can include more than two winders to allow for motion in more than one dimension (e.g., up-down in addition to side-to-side).

A sealing cartridge can also include a casing, which provides a track upon which the slider tape can move. In some cases where a sealing cartridge does not include a casing, a track can be provided by a sample manipulation chamber. A casing also provides for a seal over the access hole of a sample manipulation chamber because a casing can be attached to the sample manipulation chamber.

Figure 4:
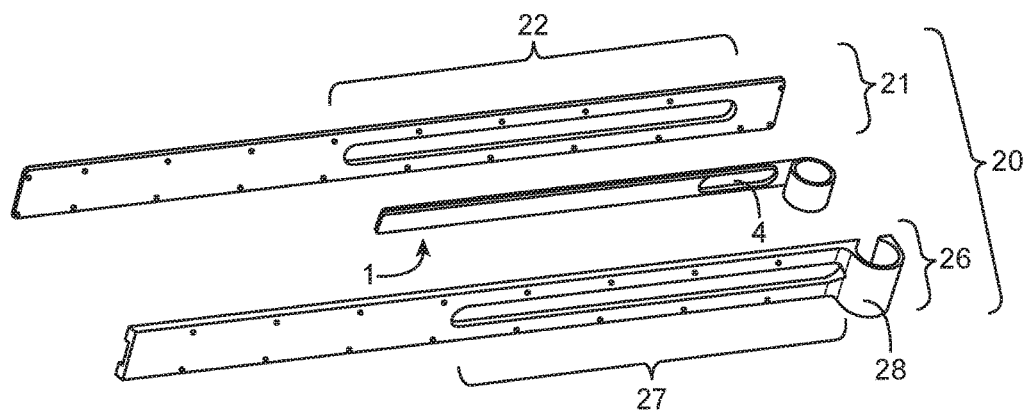
FIG. 4 depicts one embodiment of a sealing cartridge 20 that includes a back plate 21 and a front plate 26 that attach to one another to enclose a slider tape 1. The front plate 26 has a winder 28 at one end and an access hole 27. The backer plate 21 has an access hole 22.

In some cases, a sealing cartridge includes a casing that has two components (e.g., a front plate and a back plate), which attach to one another and enclose the slider tape. In some such cases, a back plate is configured to attach to the sample manipulation chamber (e.g., via any convenient fastening method, e.g., adhesive, adhesive strips, screws, caulking, etc.). Likewise, a front and a back plate can attach to one another by any convenient fastening method (e.g., snap together, adhesive, adhesive strips, screws, caulking, etc.). In some cases, a front plate includes the winder (FIG. 4). Thus, in some cases, the casing of the sealing cartridge includes a front plate and a back plate, and in some cases, the winder is part of the casing (FIG. 4).

In some cases, the casing is one piece. For example, in some cases, the casing attaches to a sample manipulation chamber (i.e., is configured to attach to a sample manipulation chamber). In some cases, a casing includes the winder, and in other cases, the casing is a separate component of the sealing cartridge.

Figure 2:
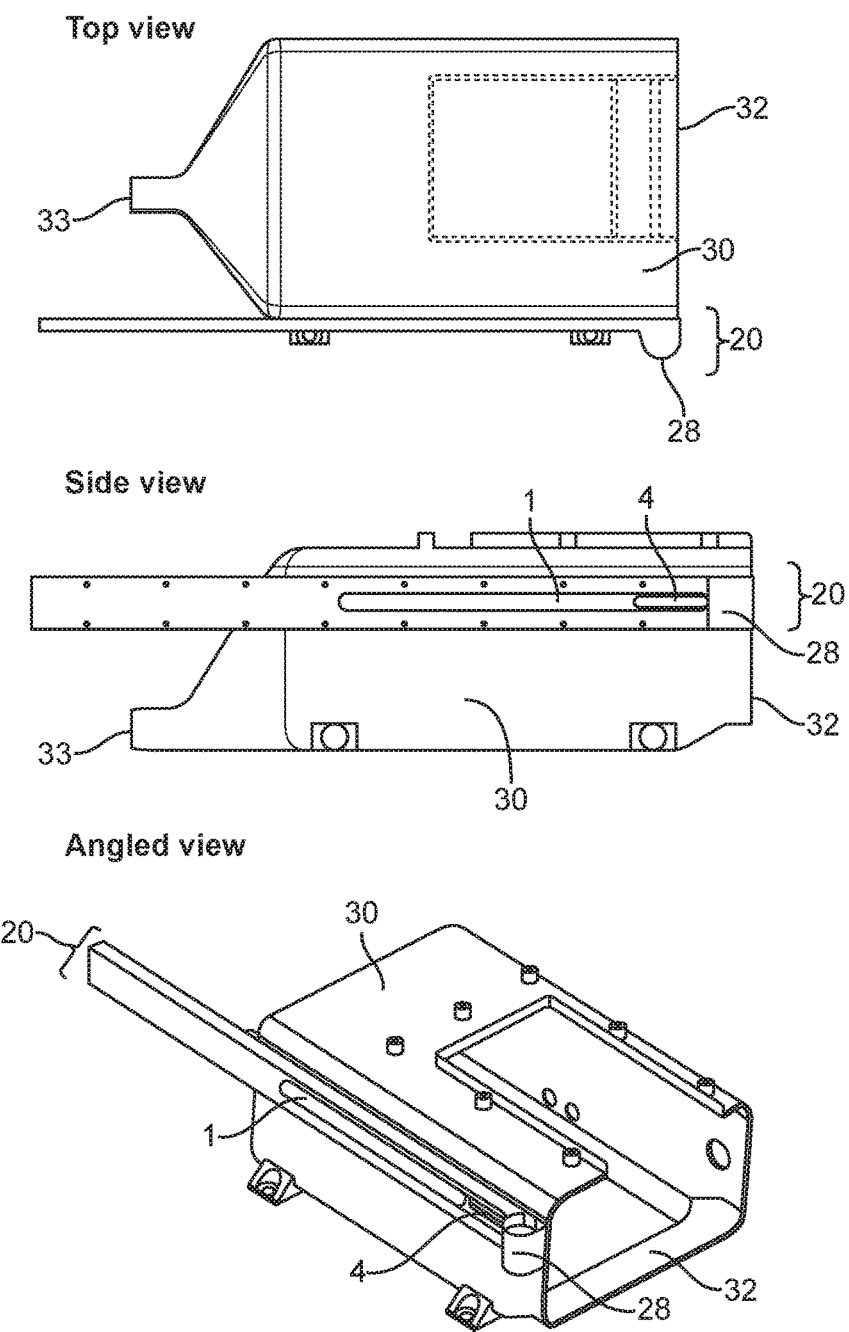
FIG. 2 depicts one embodiment of a sample manipulation chamber 30 that is adjustably sealed by an attached sealing cartridge 20, where the sealing cartridge 20 includes a slider tape 1 (having an access hole 4), and a winder 28 at one end. Also depicted are the influx opening 32 and efflux opening 33 of the sample manipulation chamber 30.

A slider tape can be completely contained within a casing or can extend beyond the casing (e.g., on an end that does not reversibly wind upon itself)(see e.g., FIG. 2). For example, if a slider tape has an end that is part of a rigid region (i.e., the end does not reversibly wind upon itself), the casing can extend as far as the slider tape can reach (which will be limited by where the access holes of the slider tape and casing align). On the other hand, the casing can be truncated on one end (e.g., the end that does not include the winder) such that the rigid region of the slider tape extends out of and beyond the casing.

The casing and/or winder of the sealing cartridge can be made of any convenient material. For example the material composition of the casing and/or winder can include metal, aluminum, steel, a metal alloy, a plastic polymer (e.g., selected from polyvinyl chloride (PVC), polystyrene, polypropylene, and the like), etc.

A sealing cartridge can be any convenient shape and size. The size and shape of a sealing cartridge will depend on multiple factors, including the shape and size of the access hole of the sample manipulation chamber, which will in turn depend on the size and shape of the sample manipulation chamber itself. A subject sealing cartridge will be of appropriate size and shape so as to cover the access hole of a sample manipulation chamber while allowing motion of the slider tape within the sealing cartridge along the length and/or width of the access hole of the sample manipulation chamber.

Sample Manipulation Chamber

A sample manipulation chamber is a chamber that encloses a region containing samples to be manipulated. For example, a particle collection region of a flow cytometer can include a sample manipulation chamber (e.g., to allow for the containment of generated aerosols). A sample manipulation chamber has an access hole through which a mobile arm can penetrate into the sample manipulation chamber. When a sample manipulation chamber has an access hole that is adjustably sealed with a subject sealing cartridge, the mobile arm can penetrate into the sample manipulation chamber by penetrating the holes of the sealing cartridge and the sample manipulation chamber. For example, a mobile arm can penetrate into the sample manipulation chamber by penetrating the access hole of the slider tape of the sealing cartridge, thereby penetrating the access hole of the sample manipulation chamber.

A mobile arm can move (e.g., laterally) relative to the sample manipulation chamber in order to manipulate samples within (e.g., by manipulating a sample collection vessel). Thus, the access hole of the sample manipulation chamber is larger than the dimensions of the mobile arm (at least for the region of the mobile arm that penetrates the sample manipulation chamber) in order to allow for lateral motion. The seal provided by a subject sealing cartridge is considered an "adjustable seal" because the sealing cartridge allows the mobile arm to move relative to the sealing cartridge and relative to the sample manipulation chamber, while maintaining a seal over the access hole of the sample manipulation chamber.

A sample manipulation chamber can include tracks upon which a subject slider tape can move. As such, in some cases, a sealing cartridge includes a winder and a slider tape, but the tracks that provide limits to the motion of the slider tape are provided by the sample manipulation chamber.

The exact dimensions and shape of the sample manipulation chamber can depend on various factors, including the desired features of the sample manipulation chamber, the size and shape of the region enclosed by the sample manipulation chamber (e.g., a particle collection region of a flow cytometer), the size and shape of an instrument with which the sample manipulation chamber is to be associated (e.g., a flow cytometer), etc. One exemplary sample manipulation chamber is 8.7 inches wide, 5 inches high, and 16.2 inches deep.

The width of a sample manipulation chamber can be any convenient width. In some cases (e.g., when the sample manipulation chamber is intended to be associated with a flow cytometer), the width of a sample manipulation chamber can be in a range of from 2 inches to 30 inches (e.g., from 2 inches to 25 inches, from 2 inches to 20 inches, from 2 inches to 15 inches, from 5 inches to 11 inches, from 6 inches to 10 inches, from 7 inches to 10 inches, or from 7 inches to 9 inches).

The height of a sample manipulation chamber can be any convenient height. In some cases (e.g., when the sample manipulation chamber is intended to be associated with a flow cytometer), the height of a sample manipulation chamber can be in a range of from 1 inch to 10 inches (e.g., from 1 inch to 9 inches, from 2 inches to 8 inches, from 3 inches to 7 inches, or from 4 inches to 6 inches).

The depth of a sample manipulation chamber can be any convenient depth. In some cases (e.g., when the sample manipulation chamber is intended to be associated with a flow cytometer), the depth of a sample manipulation chamber can be in a range of from 2 inches to 30 inches (e.g., from 2 inches to 25 inches, from 5 inches to 25 inches, from 8 inches to 24 inches, from 10 inches to 22 inches, from 12 inches to 20 inches, from 14 inches to 18 inches, or from 15 inches to 17 inches).

The volume of a sample manipulation chamber can be any convenient volume. In some cases (e.g., when the sample manipulation chamber is intended to be associated with a flow cytometer), the volume of a sample manipulation chamber can be in a range of from 0.1 cubic feet (cf) to 1 cf (e.g., from 0.2 cf to 0.9 cf, from 0.2 cf to 0.8 cf, from 0.2 cf to 0.7 cf, from 0.2 cf to 0.6 cf, or from 0.3 cf to 0.5 cf).

The exact dimensions and shape of the access hole of the sample manipulation chamber can also depend on various factors, including, the size and shape of a mobile arm that penetrates the chamber, the degree and direction of motion required by a mobile arm that penetrates the chamber, etc. The length, width, and area of the access hole are limited in that they can be any dimension that is less than or equal to the length, width, and/or area of the surface of the sample manipulation chamber with which the access hole is associated. The shape of an access hole of the sample manipulation chamber can be any convenient shape. For example, in some cases, the shape of an access hole of the sample manipulation chamber is selected from: a square, a rectangle, a rectangle with rounded corners, a pentagon, a hexagon, a polygon, an ellipse, a triangle, a trapezoid, a rhomboid, and a circle.

A sample manipulation chamber does not have to be completely sealed. For example, in some cases, a sample manipulation chamber as in influx opening and/or an efflux opening to allow fluid (e.g., air) to flow within the sample manipulation chamber. In some cases, a sample manipulation chamber has both an influx opening and an efflux opening. The size of an influx and/or efflux opening is only limited by the dimensions of the sample manipulation chamber. For example, an influx opening can simply be the absence of an entire face of the chamber (e.g., in influx opening of a sample manipulation chamber can be the entire front face)(e.g., see FIGS. 1-2 and 5-9). In some cases, an influx or efflux opening can be covered, e.g., by a filter (e.g., an air filter, discussed in more detail below). In some cases, the sample manipulation chamber is penetrated by other components of a flow cytometer (e.g., see FIG. 1B and FIG. 2).

Flow Cytometer

In some embodiments, the present disclosure provides a flow cytometer. Flow cytometry is a methodology using multi-parameter data for identifying and distinguishing between different particle types (i.e., particles, such as cells, that vary from one another in terms of label wavelength, label intensity, size, etc.) in a fluid medium. In general, a flow cytometer is made up of at least three regions: (i) a sample loading region; (ii) a particle interrogation region; and (iii) a particle collection region.

In performing flow cytometry (i.e., flow cytometrically analyzing particles of a sample), a liquid sample (containing particles to be analyzed) is first introduced into a sample loading region, which is sometimes referred to in the art as a sample injection chamber, of a flow cytometer. During sample acquisition, the chamber of the sample loading region is pressurized to force sample into the flow path of the flow cytometer, toward the particle interrogation region. Ideally, the fluid stream is at its minimum diameter so that cells pass through the laser beam of the sample interrogation region in a single-file stream. However, depending on the application, a lower resolution might be acceptable in order to acquire data more quickly.

When in the flow path, articles are passed substantially one at a time through the particle interrogation region, where each of the particles is exposed individually to an energy source (e.g., a light source) and measurements of light scatter parameters (e.g., forward scatter, side scatter, etc.) and/or fluorescent emissions as desired (e.g., one or more fluorescent emissions) are separately recorded for each particle. The energy source may include an illuminator that emits light of a single wavelength, such as that provided by a laser (e.g., He/Ne or argon) or a mercury arc lamp with appropriate filters. Examples of excitation light sources include lasers, light emitting diodes, and arc lamps. For example, light at 488 nm may be used as a wavelength of emission in a flow cytometer having a single sensing region. For flow cytometers that emit light at two or more distinct wavelengths, additional wavelengths of emission light may be employed, where specific wavelengths of interest typically include, but are not limited to: 535 nm, 635 nm, and the like. A subject flow cytometer can have one or more lasers (e.g., two or more, three or more, four or more, five or more, six or more, etc.).

In the particle interrogation region, detectors (e.g., light collectors, such as photomultiplier tubes (or "PMT")), are used to record light that passes through each particle (generally referred to as forward light scatter), light that is reflected orthogonal to the direction of the flow of the particles through the sensing region (generally referred to as orthogonal or side light scatter) and fluorescent light emitted from the particles, if it is labeled with fluorescent marker(s), as the particle passes through the sensing region and is illuminated by the energy source. Each of forward light scatter (or FSC), orthogonal light scatter (SSC), and fluorescence emissions (FL1, FL2, etc.) comprise a separate parameter for each particle (or each "event"). Thus, for example, two, three or four parameters can be collected (and recorded) from a particle labeled with two different fluorescence markers.

The data recorded for each particle is analyzed in real time and/or stored in a data storage and analysis device, such as a computer, as desired. Publications from the scientific and patent literature describing various designs, configurations, and uses of flow cytometers include, for example: (i) Jaye et al., J. Immunol. 2012 May 15; 188(10):4715-9: Translational applications of flow cytometry in clinical practice; (ii) Krutzik et al., Curr Protoc Cytom. 2011 January; Chapter 6: Unit 6.31: Fluorescent cell barcoding for multiplex flow cytometry; (iii) Black et al., Assay Drug Dev Technol. 2011 February; 9(1):13-20: Cell-based screening using high-throughput flow cytometryl (iv) Abayomi et al., Cytometry B Clin Cytom. 2008; 74 Suppl 1: S80-9: Flow cytometry as the spearhead for delivering sustainable and versatile laboratory services to HIV-burdened health care systems of the developing world: a Caribbean model; (v) Snow et al., Cytometry A. 2004 February; 57(2):63-9: Flow cytometer electronics; (vi) Schmid et al., Cytometry A. 2003 December; 56(2):113-9: Biosafety concerns for shared flow cytometry core facilities; and (vii) U.S. Pat. Nos. 8,502,976, 8,486,371, 8,441,637, 8,441,624, 7,990,525, 8,021,872, 7,611,849, and 7,354,773; all of which citations are hereby incorporated by reference in their entirety.

Any convenient flow cytometer is suitable for use in a subject flow cytometer system, and an appropriate flow cytometer will be based on the desired features of the flow cytometer. For example, some flow cytometers are designed to interrogate particles for various characters (e.g., forward light scatter, side light scatter, fluorescence, etc.), but cannot sort the particles as they flow through the machine. Some flow cytometers are equipped to sort particles as they flow through the machine, redirecting the particle (after the particle has been interrogated/evaluated) to a particular location (e.g., into a desired sample collection container).

During sorting, the fluid stream is broken into highly uniform droplets, which detach from the stream. The time between when a particle intercepts the energy source (e.g., the laser) and when it reaches the droplet breakoff point is determined. When a particle is detected that meets the predefined sorting criteria, an electrical charge is applied to the stream just as the droplet containing that particle breaks off from the stream. Once broken off from the stream, the droplet—now surrounded by air—retains its charge. The charged droplet passes by two strongly charged deflection plates. Electrostatic attraction and repulsion cause each charged droplet to be deflected to the left or right, depending on the droplet's charge polarity. For example, in some cases, a flow cytometer can sort particles into one of two different tubes, or into a desired well of a multi-well plate (e.g., a 6-well plate, a 12-well plate, a 24-well plate, a 48-well plate, a 96-well plate, etc.). Uncharged droplets are not affected by the electric field and pass down the center to be collected or aspirated as waste. Thus, a flow cytometer can include a deflection plate, e.g., 1 or more deflection plates (e.g., 2 or more, 3 or more, 4 or more, 5 or more, etc.), which can alter the course of charged droplets (e.g., by being charged to various degrees and/or in various arrangements relative to one another when more than one deflection plate is present).

Examples of suitable flow cytometers include, but are not limited to flow cytometers manufactured by Becton, Dickinson and Company, including: BD ACCURI™ C6, BD FACSCANTO™, BD FACSVERSE™, BD LSR-FORTESSA™ X-20, BD LSRFORTESSA™, BD INFLUX™, BD FACSJAZZ™, BD FACSARIA™ (e.g., BD FACSARIA™ III), and the flow cytometer provided with the BD FACSARIA™ Fusion.

Regardless of the type of flow cytometer, the term "particle collection region" as used herein refers to the region of the flow cytometer where the flow path comes to an end. In some cases, particles are sorted and/or collected in the particle collection region. In some cases, particles are collected as waste or discarded (e.g., aspirated) in the particle collection region.

In some cases, a particle collection region includes a sample collection vessel (e.g., a tube). Any convenient sample collection vessel can be used. For example, in some cases, a particle collection region includes one or more sample collection tubes (e.g., a single collection tube, 2 or more collection tubes, 3 or more collection tubes, 4 or more collection tubes, 5 or more collection tubes, 6 or more collection tubes, 12 or more collection tubes, 24 or more collection tubes, 48 or more collection tubes, 96 or more collection tubes, 384 or more collection tubes, 1,536 or more collection tubes, etc.). In some cases, a sample collection vessel is a multi-well plate (e.g., a 6-well plate, a 12-well plate, a 24-well plate, a 48-well plate, a 96-well plate, a 384-well plate, a 1,536-well plate, etc.).

In some embodiments, a flow cytometer includes a mobile arm that penetrates into the particle collection region (e.g., by penetrating a surrounding sample manipulation chamber). When a sample manipulation chamber has an access hole that is adjustably sealed with a subject sealing cartridge, the mobile arm can penetrate into the sample manipulation chamber by penetrating the holes of the sealing cartridge and the sample manipulation chamber (e.g., by penetrating the access hole of the slider tape). In some cases, the mobile arm is configured to manipulate samples in the sample manipulation chamber. In some cases, the mobile can be configured to manipulate a sample collection vessel, e.g., one or more sample collection vessels (2 or more, 3 or more, 4 or more, etc.), within the sample collection chamber. For example, in some cases, a mobile arm can support (and in some cases secure) an associated sample collection vessel. In some cases, a mobile arm can attach to a sample collection vessel. Thus, when the mobile arm moves, it moves the sample collection vessel. Such an arrangement can allow for the sorting of many different particle types into many different sample collection vessels.

In some cases, the mobile arm is an automated (i.e., robotic) arm. As described above regarding a sample manipulation chamber, a mobile arm can move relative to the sample manipulation chamber in order to manipulate samples, and thus, the access hole of the sample manipulation chamber is larger than the dimensions of the mobile arm (at least for the region of the mobile arm that penetrates the sample manipulation chamber).

While aerosols may be generated anywhere along the flow path of a flow cytometer, the majority of aerosols tend to be generated in the particle collection region. Thus, in some embodiments, the particle collection region is configured to fluidically couple (e.g., via a conduit, such as a hose, a tube, flexible ducting, etc.) to a dedicated air filtration system referred to herein as an aerosol management system (AMS) (described in more detail above). In some such cases, the particle collection region is enclosed (e.g., in some cases, airtight) in a chamber (e.g., a sample manipulation chamber) (FIG. 7B, FIG. 8, and FIG. 9) (i.e., the particle collection region can include a sample manipulation chamber). The sample manipulation chamber can be air-tight and/or can be completely enclosed, with various possible exceptions, including: (i) there can be a filter on one side to allow clean air into the sample chamber (e.g., through the influx opening); (ii) there can be an efflux opening on one side (e.g., that can be fluidically coupled to an AMS, e.g., the opening can be connected to a conduit, e.g., a hose, flexible tubing, flexible ducting, etc., that can connect to an AMS (FIG. 8), which can generate air flow); (iii) there can be an access hole that is adjustably sealed by a subject sealing cartridge, which is configured to allow a mobile arm to adjustably penetrate through the sealing cartridge into the sample manipulation chamber; and (iv) there can be an opening to allow the flow path of the flow cytometer to enter the sample manipulation chamber (e.g., on top of the sample manipulation chamber, as depicted in FIG. 1B, FIG. 5B, FIG. 6B, and FIG. 7B).

Figure 7A:
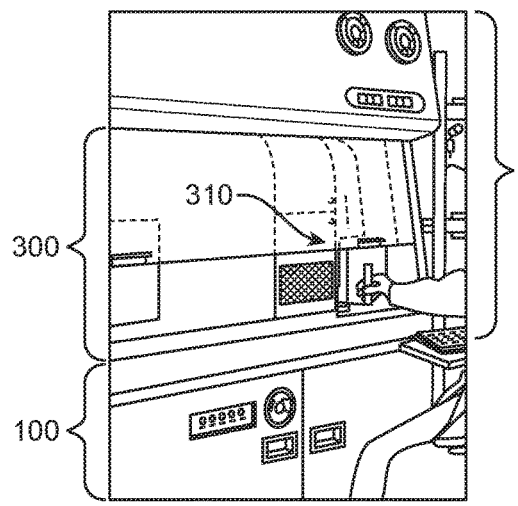
FIG. 7A-7D depicts various components and various embodiments of a flow cytometer system.
Figure 7B:
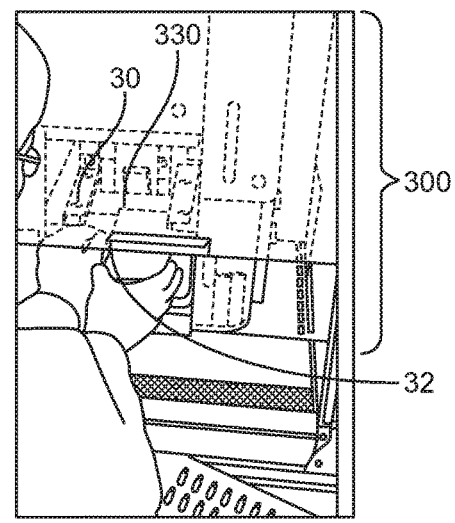

When an associated AMS is actuated, gas (e.g., ambient air, decontamination gas, etc.), in some cases containing aerosols, flows from the filter side of the sample chamber (e.g., from the influx opening) to the side where the sample chamber is fluidically coupled to the AMS (e.g., the efflux opening, FIG. 9). Thus, in some cases, the sample manipulation chamber encloses a particle collection region that is a mini-environment such that aerosols within the particle collection region are contained and can be carried away by airflow generated by the air filtration system of the AMS. In some embodiments, an air-tight sample chamber of the particle collection region can be opened (e.g., via a hinged door, a sliding door, etc.) to allow operator access to the sample chamber (e.g., to recover sorted samples, for cleaning, to allow gas exposure during decontamination procedures, etc.) (FIG. 7B).

One non-limiting example of a flow cytometer having a particle collection region configured to fluidically couple to an aerosol management system of a biosafety hood is the flow cytometer provided with the BD FACSARIA™ Fusion, which is commercially available from Becton, Dickinson and Company.

Figure 7C:
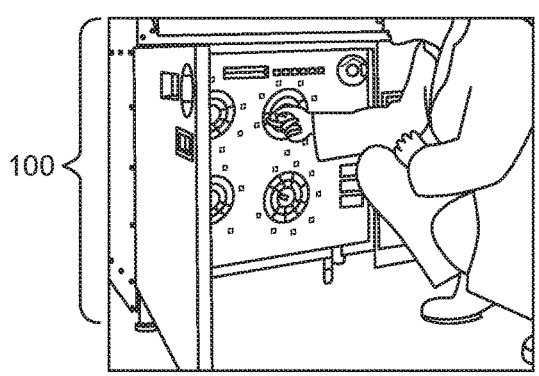

In some embodiments, a flow cytometer has non-aerosol generating components that are not part of the sample flow path and are not contained by the enclosure of the BSH. For example, components such as spectral filters, lasers, detector arrays, etc. can be housed outside of the enclosure of the BSH. For example, in some embodiments, a flow cytometer instrument base contains non-aerosol generating components (e.g., spectral filters, lasers, detector arrays, and the like) of an associated flow cytometer (FIG. 7C).

The exact dimensions and shape of the flow cytometer will depend on the desired features of the flow cytometer. In some cases, the exact dimensions will also depend on the dimensions and shape of the BSH and/or instrument base with which the flow cytometer is to be associated.

In some embodiments, the volume of the flow cytometer (i.e., the volume occupied) can be in a range of from 15 cubic feet (cf) to 60 cf (e.g., 15 cf to 50 cf, 15 cf to 40 cf, 15 cf to 35 cf, 15 cf to 30 cf, 17.5 cf to 35 cf, 17.5 cf to 30 cf, 17.5 cf to 27.5 cf, 17.5 cf to 25 cf, or 20 cf to 22.5 cf).

In some embodiments, the height of the flow cytometer can be in a range of from 1 foot (ft) to 6 feet (ft) (e.g., from 1.5 ft to 5 ft, from 1.5 ft to 4 ft, from 1.5 ft to 3 ft, from 1.5 ft to 2.5 ft, from 2 ft to 5 ft, from 2 ft to 4 ft, from 2 ft to 3 ft, from 2 ft to 2.5 ft, 2 ft, 2.1 ft, 2.2 ft, 2.3 ft, 2.4 ft, 2.5 ft, 3 ft, 4 ft, or 5 ft).

In some cases, the width of the flow cytometer can be in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2.5 ft to 9 ft, from 2.5 ft to 8 ft, from 2.5 ft to 7 ft, from 2.5 ft to 6 ft, from 2.5 ft to 5 ft, from 2.5 ft to 4.5 ft, from 2.5 ft to 4 ft, from 3 ft to 9 ft, from 3 ft to 8 ft, from 3 ft to 7 ft, from 3 ft to 6 ft, from 3 ft to 5 ft, from 3 ft to 4.5 ft, from 3 ft to 4 ft, from 3.5 ft to 9 ft, from 3.5 ft to 8 ft, from 3.5 ft to 7 ft, from 3.5 ft to 6 ft, from 3.5 ft to 5 ft, from 3.5 ft to 4.5 ft, from 3.5 ft to 4 ft, 2 ft, 3 ft, 3.5 ft, 4 ft, 4.5 ft, 5 ft, 6 ft, 7 ft, 8 ft, 9 ft, or 10 ft).

In some cases, the depth of the flow cytometer can be in a range of from 1 foot (ft) to 6 feet (ft) (e.g., from 1.5 ft to 5 ft, from 1.5 ft to 4 ft, from 1.5 ft to 3 ft, from 1.5 ft to 2.5 ft, from 2 ft to 5 ft, from 2 ft to 4 ft, from 2 ft to 3 ft, from 2 ft to 2.5 ft, 2 ft, 2.1 ft, 2.2 ft, 2.3 ft, 2.4 ft, 2.5 ft, 3 ft, 4 ft, or 5 ft).

Biosafety Hood (BSH)

In some embodiments, the present disclosure provides a biosafety hood (BSH). The term "hood" is used herein to refer to an enclosure or canopy provided with a draft (i.e., air flow) for carrying off aerosols, fumes, sprays, smokes, or dusts. A "biosafety hood" is therefore a hood intended to facilitate the safe handling of biologically related materials (e.g., aerosols containing dangerous, toxic, and/or infectious particles, etc.). In some instances, the BSH is configured to keep aerosols from escaping. In some instances, the BSH is configured to maintain purity of the materials being analyzed/sorted by the flow cytometer. As such, in some instances the BSH is configured to keep both particles from escaping the interior of the BSH as well as entering the interior of the BSH.

A subject BSH is designed to form an enclosure (referred to herein as the "main enclosure") that can enclose a flow cytometer. The exact dimensions and shape of the BSH (and the main enclosure) therefore depend on the dimensions and shape of the flow cytometer to be enclosed. The BSH (and the main enclosure) can be of any convenient shape (e.g., dome-like, sphere-like, cube-like, cuboid-like, cylinder-like, pyramid-like, cone-like, hexagonal prism-like, triangular prism-like, etc.). As described below, a BSH can include all sides/surfaces of its shape, or a BSH can be missing one or more sides or surfaces.

In some embodiments, the BSH can have greater overall dimensions than the main enclosure (described below) that the BSH defines. For example, the BSH can include an additional compartment, separate from (and not enclosed by) the main enclosure. In some cases, a BSH has a region (e.g., an upper region) that can house any convenient component, e.g., an air filtration system, a fan, a blower assembly, ducting, hoses, conduits, a processor, an aerosol management system (AMS), etc. In some such cases, therefore, the dimensions (e.g., height, width, and/or depth) of the BSH are greater than the dimensions of the main enclosure that the BSH defines.

In some embodiments, the height of the BSH can be in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the BSH can enclose a flow cytometer, the height of the BSH is greater than the height of the flow cytometer to be enclosed. In some cases, the height of the BSH can be in a range of from 100.05% to 250% the height of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some cases, the width of the BSH can be in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the BSH can enclose a flow cytometer, the width of the BSH is greater than the width of the flow cytometer to be enclosed. In some cases, the width of the BSH can be in a range of from 100.05% to 250% the width of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some cases, the depth of the BSH can be in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the BSH can enclose a flow cytometer, the depth of the BSH is greater than the depth of the flow cytometer to be enclosed. In some cases, the depth of the BSH can be in a range of from 100.05% to 250% the depth of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 122.5%, from 100.05% to 120%, from 100.05% to 115%, from 100.05% to 110%, from 100.05% to 107.5%, from 100.05% to 105%, or from 100.05% to 102.5%).

Enclosure.

A suitable BSH can attach to a flow cytometer instrument base (described in more detail below) such that an enclosure exists (the 'main enclosure') that is large enough to contain a flow cytometer. Thus, in some cases, an instrument base is configured to attach to a BSH, and/or a BSH is configured to attach to an instrument base. By "configured to attach" is meant that a component is designed in such a way as to facilitate attachment to another component. For example, in some cases, "configured to attach" can mean that at least a portion of a surface of a first component is flat, thus allowing adhesion to the surface of a second component. As another example, in some cases, "configured to attach" can mean that a first component can have holes, tabs, ridges, slots, etc. to allow the first component to attach to a second component. How a particular component is "configured to attach" to another component can depend, for example, on how the two components are to be attached (e.g., screws, bolts, clips, adhesive, sealant, etc.).

The exact dimensions (and shape) of the main enclosure will depend on the dimensions and shape of the flow cytometer to be enclosed. However, because the main enclosure is designed to contain a flow cytometer, the volume of the main enclosure is equal to or greater than the volume to be occupied by the flow cytometer. In order to reduce the overall footprint of a subject flow cytometer system, the volume of the main enclosure is designed to be small relative to the volume occupied by the flow cytometer to be enclosed.

In some embodiments, the volume of the main enclosure (i.e., the volume enclosed) can be in a range of from 15 cubic feet (cf) to 60 cf (e.g., 15 cf to 50 cf, 15 cf to 40 cf, 15 cf to 35 cf, 15 cf to 30 cf, 17.5 cf to 35 cf, 17.5 cf to 30 cf, 17.5 cf to 27.5 cf, 17.5 cf to 25 cf, 17.5 cf to 22.5 cf, 20 cf to 25 cf, 20 cf to 22.5 cf, 21 cf to 22 cf, or 22 cf to 25 cf). In some cases, the volume of the main enclosure can be in a range of from 100.05% to 200% the volume occupied by the flow cytometer to be enclosed (e.g., from 100.05% to 190%, from 100.05% to 180%, from 100.05% to 170%, from 100.05% to 160%, from 100.05% to 150%, from 100.05% to 145%, from 100.05% to 140%, from 100.05% to 135%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some embodiments, the height of the main enclosure can be in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the main enclosure is designed to contain a flow cytometer, the height of the main enclosure is equal to or greater than the height of the flow cytometer to be enclosed. In some cases, the height of the main enclosure can be in a range of from 100.05% to 250% the height of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some cases, the width of the main enclosure can be in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the main enclosure is designed to contain a flow cytometer, the width of the main enclosure is equal to or greater than the width of the flow cytometer to be enclosed. In some cases, the width of the main enclosure can be in a range of from 100.05% to 250% the width of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some cases, the depth of the main enclosure can be in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the main enclosure is designed to contain a flow cytometer, the depth of the main enclosure is equal to or greater than the depth of the flow cytometer to be enclosed. In some cases, the depth of the main enclosure can be in a range of from 100.05% to 250% the depth of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 122.5%, from 100.05% to 120%, from 100.05% to 115%, from 100.05% to 110%, from 100.05% to 107.5%, from 100.05% to 105%, or from 100.05% to 102.5%).

In some embodiments, the main enclosure is defined by a combination of surfaces of the BSH and the instrument base. Thus, in such cases, the BSH does not include all of the surfaces that define the main enclosure. For example, the BSH may not include one or more of: a bottom surface (i.e., a floor), a back surface, and/or a side surface, such that the missing surface(s) can be provided by the instrument base. For example, in some cases, the BSH does not include a floor, and the bottom surface of the main enclosure is therefore defined by an upward-facing surface of the instrument base. In some cases, the BSH has a bottom surface such that the bottom surface of the main enclosure is defined by the bottom surface of the BSH. In some such cases, the bottom surface of the BSH attaches to a surface (e.g., an upward facing surface) of the instrument base. In some cases, all surfaces of the main enclosure are defined by the BSH. For example, in some cases, a subject BSH includes a floor, a ceiling, and all sides (e.g., a front, a back, and sides).

Any convenient type of attachment (e.g., bolts, clamps, pegs, latches, screws, magnets, adhesives, sealants and the like) can be used to attach an instrument base to a BSH. In some cases (e.g., in embodiments where at least one surface of the main enclosure is defined by the instrument base), the BSH and the instrument base are attached such that they form a seal to prevent aerosols from escaping the main enclosure at the site(s) of attachment. Any convenient method/substance can be used to form a seal. In some cases, a gasket (e.g., a rubber gasket) is used. In some cases, a sealant is used. Any of a wide variety of sealants can be used, and the selection of a sealant will generally depend on the material makeup of the BSH and the instrument base, as well as the type of aerosols and/or gases (e.g., decontamination gas) to which the sealant may be exposed. Examples of suitable sealants include, but are not limited to: silicon sealants, acrylic sealants, adhesive sealants, epoxy sealants, foam sealants, gasket sealants, glass sealants, impregnating sealants, latex sealants, metal sealants, plastic sealants, polysulfide sealants, polyurethane sealants, rubber sealants, seam sealants, urethane sealants, etc.

In some embodiments, a flow cytometer has non-aerosol generating components that are not part of the sample flow path and are not contained by the main enclosure of the BSH. For example, components such as spectral filters, lasers, detector arrays, etc. can be housed outside of the main enclosure of the BSH. For example, in some embodiments, a flow cytometer instrument base contains non-aerosol generating components of an associated flow cytometer (FIG. 7C). Thus, for example, the phrase "the flow cytometer is present in an enclosure defined by the BSH and the flow cytometer instrument base" does not mean that all components of the flow cytometer are necessarily contained within the main enclosure. Instead, such a phrase means that at least the flow path (i.e., the potential aerosol generating components: the sample loading region, the particle interrogation region, and the particle collection region) of the flow cytometer is present in the main enclosure.

Air Filtration System(s).

A subject BSH has at least one air filtration system, referred to herein as a "main" air filtration system or a "first" air filtration system. An air filtration system is used to remove hazardous materials (e.g., infectious particles and/or toxins, hazardous chemicals, etc.) via air flow. The main (first) air filtration system of a BSH removes aerosols from the main enclosure. In some cases, an air filtration system is fluidically coupled to a sample manipulation chamber (e.g., air can traverse into a sample manipulation chamber through the influx opening, and out through an efflux opening).

An air filtration system includes a blower to generate air flow. The term "blower" or "blower assembly" is used herein to refer to any type of device that can be used to generate air flow (e.g., using a fan mechanism, using a turbine-based mechanism, using a bellows-based mechanism, etc.). Any convenient type of blower may be used that generates an appropriate amount of air flow as desired. In some embodiments, a blower includes a fan. In some embodiments, the speed of air flow generated by the blower can be controlled by a user (e.g., via an instrument control panel associated with the BSH, via a processor that can control the blower, etc.).

In some embodiments, the blower of any one or more air filtration systems (e.g., the main blower, i.e., the blower of the main air filtration system; the AMS blower, i.e., the blower an aerosol management system; etc.) can operate at two or more speed settings (e.g., low (LO), medium (MED), and/or high (HI)). Speed settings can be set for any convenient speed (e.g., 5 cubic feet per minute (cfm), 10 cfm, 15 cfm, 20 cfm, 25 cfm, 30 cfm, 35 cfm, 40 cfm, 45 cfm, 50 cfm, 55 cfm, 60 cfm, 65 cfm, 70 cfm, 75 cfm, 80 cfm, 85 cfm, 90 cfm, 95 cfm, 100 cfm, 105 cfm, 110 cfm, 115 cfm, 120 cfm, 125 cfm, 130 cfm, 135 cfm, 140 cfm, 145 cfm, 150 cfm, 155 cfm, 160 cfm, 165 cfm, etc.). In some cases, a blower can be controlled by a variable speed setting. For example, in some cases, speed settings can range from 5 cubic feet per minute (cfm) to 300 cfm (from 10 cfm to 200 cfm, from 10 cfm to 150 cfm, from 10 cfm to 100 cfm, from 10 cfm to 80 cfm, from 10 cfm to 60 cfm, from 10 cfm to 50 cfm, from 10 cfm to 40 cfm, or from 15 cfm to 40 cfm).

In some embodiments, an air filtration system has an air filter (to filter particles from the air). Any convenient air filter may be used. The choice of filter will depend on various factors that may include desired level of filtration, ease of maintenance, cost, etc. Examples of suitable filters include, but are not limited to: high efficiency particulate air (HEPA) filters (also sometimes referred to as high efficiency particulate arrestance filters, high efficiency particulate absorbing filters, etc.), activated carbon air filters, polyester and pleated filters, fiberglass filters, ionic air filters (i.e., air ionizers), UV light air filters, and the like.

In some embodiments, the air filter is a HEPA filter, which is a filter designed to remove particulates, including microorganisms and infectious agents, from the air. HEPA filters are available from numerous commercial sources, are available in many different shapes and sizes, and can be designed to fit almost any device that utilizes air flow (e.g., vacuum cleaners, household air filters, automobiles, biomedical devices, etc.). To be classified as a HEPA filter, a filter must satisfy certain standards of efficiency such as those set by the United States Department of Energy (DOE). To qualify as HEPA, an air filter must remove (from the air that passes through) a minimal percent of particles that have a diameter of 0.3 μm. In some cases, medical-use HEPA filtration systems also incorporate high-energy ultra-violet light units to kill off the live bacteria and viruses trapped by the filter media. Some of the highest-rated HEPA units have an efficiency rating of 99.995%, which assures a very high level of protection against airborne disease transmission. Thus, in some embodiments, a subject HEPA filter is accompanied by a high-energy ultra-violet light unit that can be used to kill off trapped particles (e.g., bacteria, fungi, viruses, etc.). In some embodiments, a subject HEPA filter has an efficiency rating of 99.5% or more (e.g., 99.7% or more, 99.8% or more, 99.9% or more, 99.92% or more, 99.93% or more, 99.94% or more, 99.95% or more, 99.96% or more, 99.97% or more, 99.98% or more, 99.99% or more, 99.995% or more, 99.9995% or more, 99.99995% or more, or 99.999995% or more).

The air filter may be positioned anywhere along the path of air flow that is generated by the blower of the air filtration system (e.g., at the beginning, at the end, or anywhere between). In some cases, the air filter is positioned at a convenient location for removal, cleaning, and/or replacement by an operator (i.e., user). In some cases, an air filtration system does not have an air filter. In such cases, aerosols can be removed from the BSH by flowing them out of the BSH (e.g., using the air flow generated by the blower) without filtration.

Figure 8A:
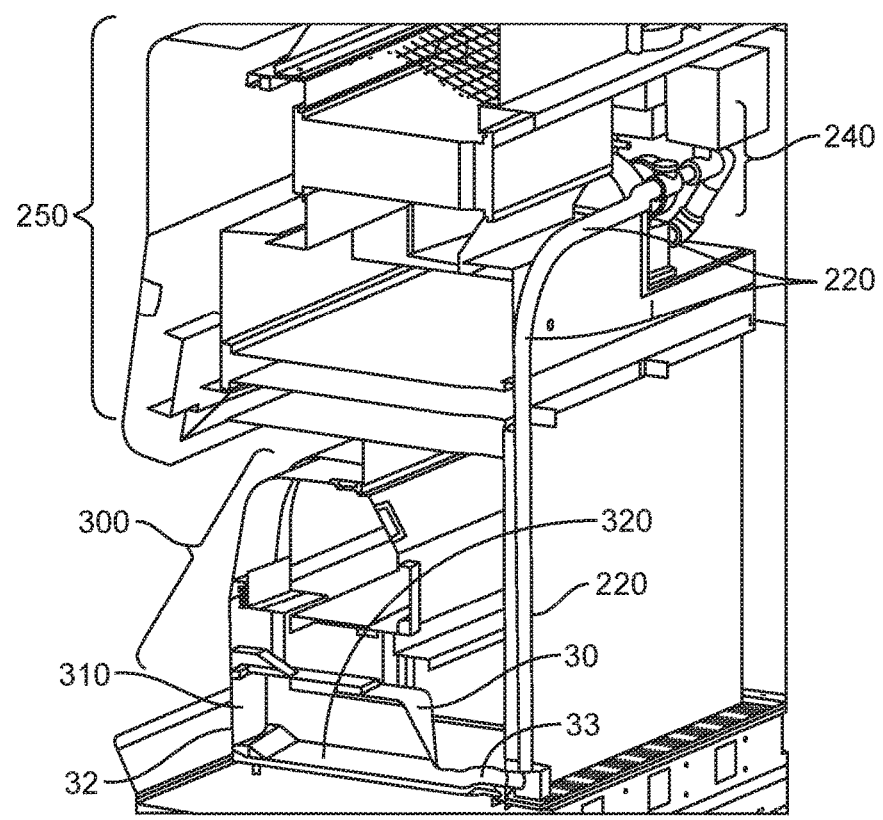
FIG. 8A-8B depict a cutaway schematic of one embodiment of a biosafety hood (BSH) having an aerosol management system (AMS) 240 that is fluidically coupled via conduit 220 to the efflux opening 33 of a sample manipulation chamber 30 of a particle collection region 320 of a flow cytometer 300. The particle collection region 320 has an air filter 310 covering an influx opening 32 (of the sample manipulation chamber 30), which is facing toward the front of the flow cytometer 300. The BSH depicted has an upper region that houses first and a second air filtration systems 250.
Figure 8B:
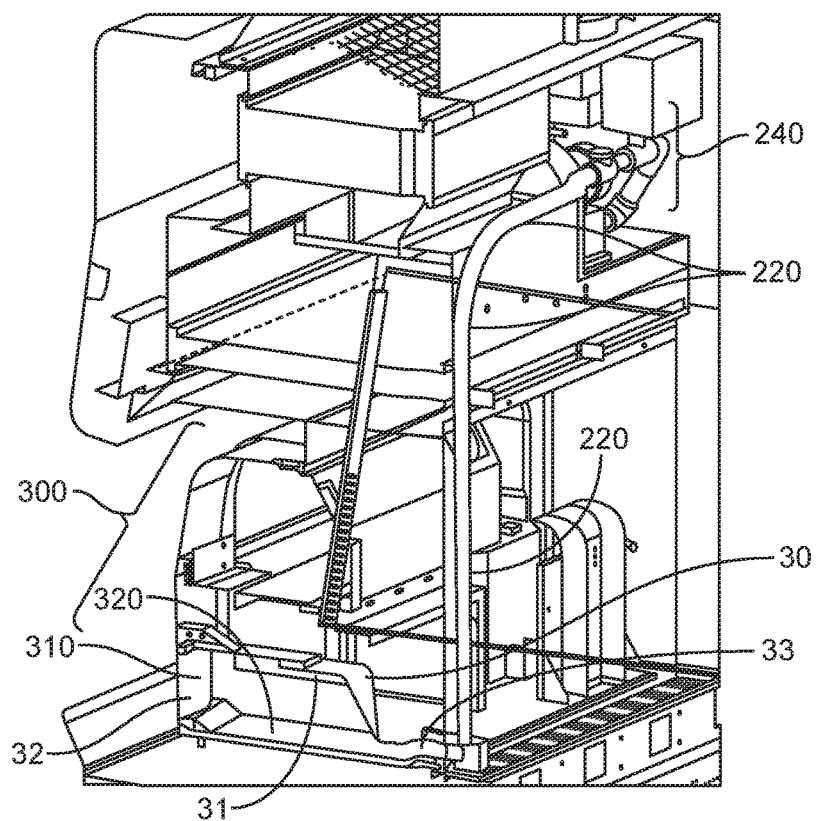

A blower assembly and/or air filter can be positioned in a region (e.g., an upper region) of the BSH that is not encapsulated by the main enclosure (i.e., the enclosure that is present when the BSH and instrument base are attached). Such a region (e.g., an upper region) can house any convenient component, e.g., an air filtration system, a fan, a blower assembly, ducting, hoses, conduits, a processor, an aerosol management system (AMS), etc. (FIG. 8).

In some embodiments, the BSH includes an opening on one surface (e.g., a forward facing surface) that can be closed and/or sealed. For example, a BSH can have a movable panel (e.g., a sliding or hinged panel, referred to in the art as a "sash") that allows operator entry into the enclosure. The term "sash" (or "hood sash") refers to the movable front face of a subject BSH, usually in glass, usually capable of upward and downward movement (or side-to-side movement), often by virtue of a counterbalance mechanism. A sash acts as a physical barrier that helps to maintain a particulate-free environment and laminar air flow. A sash can be made of any convenient material, including a transparent or translucent material (e.g., glass, plastic, a durable thermoplastic, an impact and temperature resistant polymer such as LEXAN, and the like) to allow visualization of the contents of the enclosure when the sash is closed. In some cases, a movable panel (e.g., sash) can be closed and sealed Aerosol Management System (AMS).

In some embodiments, a BSH includes a first air filtration system and an Aerosol Management System (AMS). An AMS includes an air filtration system. Thus, a BSH having an AMS includes a first (main) air filtration system and a second (AMS) air filtration system.

While aerosols may be generated anywhere along the flow path of a flow cytometer, the majority of aerosols tend to be generated in the particle collection region. Thus, in some embodiments, an AMS can fluidically couple to the flow path, or to a region of the flow path, of a flow cytometer. In some embodiments, an AMS can fluidically couple (e.g., via a conduit, such as a hose, a tube, flexible ducting, etc.) to a particle collection region of a flow cytometer. For example, in some cases, an AMS can fluidically couple to a sample manipulation chamber (e.g., via an efflux opening). The air filtration system of the AMS can therefore be referred to as being "dedicated" to the particle collection region (e.g., sample manipulation chamber) with which it is coupled.

In some such cases, the particle collection region is enclosed (e.g., in some cases, airtight) in a chamber (e.g., a sample manipulation chamber) (FIG. 7B, FIG. 8, and FIG. 9) (i.e., the particle collection region can include a sample manipulation chamber). The sample manipulation chamber can be air-tight and/or can be completely enclosed, with various possible exceptions, including: (i) there can be a filter on one side to allow clean air into the sample chamber (e.g., through the influx opening); (ii) there can be an efflux opening on one side (e.g., that can be fluidically coupled to an AMS, e.g., the opening can be connected to a conduit, e.g., a hose, flexible tubing, flexible ducting, etc., that can connect to an AMS (FIG. 8), which can generate air flow); (iii) there can be an access hole that is adjustably sealed by a subject sealing cartridge, which is configured to allow a mobile arm to adjustably penetrate through the sealing cartridge into the sample manipulation chamber; and (iv) there can be an opening to allow the flow path of the flow cytometer to enter the sample manipulation chamber (e.g., on top of the sample manipulation chamber, as depicted in FIG. 1B, FIG. 5B, FIG. 6B, and FIG. 7B).

When the AMS is actuated, gas (e.g., ambient air, decontamination gas, etc.), in some cases containing aerosols, flows from the filter side of the sample manipulation chamber (e.g., the influx opening) to the side where the sample chamber is fluidically coupled to the AMS (e.g., the efflux opening) (FIG. 9). Thus, in some cases, the sample manipulation chamber defines a mini-environment such that aerosols within the chamber are contained and can be carried away by airflow generated by the air filtration system of the AMS. In the example just described, air flows from the sample manipulation chamber to the blower of the AMS. However, (e.g., ambient air, decontamination gas, etc.) can flow in any direction so that aerosols are removed from the targeted region (e.g., the sample chamber or particle collection region). Thus, in some embodiments, air flows from the sample manipulation chamber to the blower of the AMS; and in some embodiments, air flows from the blower of the AMS to the sample manipulation chamber. Various arrangements (e.g., arrangements of blower(s), filter(s), and/or particle collection region(s)) are contemplated and an appropriate arrangement will be based on the desired outcome.

Because the AMS, when present, is a component of the BSH, the dimensions of the AMS are smaller than the dimensions of the BSH, and the exact dimensions and shape of the AMS depend on the dimensions and shape of the BSH. In some cases, the AMS is housed in the BSH (e.g., in an upper region). In some cases, the blower of the AMS is housed in the BSH (e.g., in an upper region) while an associated filter is positioned elsewhere (e.g., behind the main enclosure, inside of the main enclosure, below the main enclosure, etc.). In some cases, the overall volume occupied by the AMS is 20% or less the overall volume occupied by the BSH (e.g., 17.5% or less, 15% or less, 12.5% or less, 10% or less, 7.5% or less, 6% or less, 5% or less, 4% or less, 3% or less, 2% or less, or 1% or less).

The term "fluidically couple" is used herein to mean the coupling of components such that the components are in fluid communication with one another. Thus, two components that are in fluid communication with one another are "fluidically coupled." "Fluids" are liquids and/or gases. For example, two components that are each attached to opposite ends of a hose, where the two components are in fluid communication with one another, are "fluidically coupled" to one another. In cases where a valve is used to restrict flow of a fluid to a particular direction, the two components are still considered to be fluidically coupled. Fluidically coupled components can be coupled in any convenient way. For example, two components can be fluidically coupled directly to one another, or can be fluidically coupled via a conduit (e.g, a hose, a tube, flexible ducting, etc.).

As noted above, in some embodiments, a BSH includes a first (main) air filtration system and an AMS, where the AMS includes a second air filtration system. In some such cases, first and second air filtration systems can be controlled together (e.g., the blower (on/off, speed, etc.) for each can be controlled with the same control). In some embodiments the control can be found on an instrument control panel of the BSH. In some embodiments, the control can be found on an associated processor (e.g., a computer). In some embodiments, the blower of the AMS can operate at two or more speed settings (e.g., low (LO), medium (MED), and/or high (HI)). Speed settings can be set for any convenient speed (e.g., 5 cubic feet per minute (cfm), 10 cfm, 15 cfm, 20 cfm, 25 cfm, 30 cfm, 35 cfm, 40 cfm, 45 cfm, 50 cfm, 55 cfm, 60 cfm, 65 cfm, 70 cfm, 75 cfm, 80 cfm, 85 cfm, 90 cfm, 95 cfm, 100 cfm, 105 cfm, 110 cfm, 115 cfm, 120 cfm, 125 cfm, 130 cfm, 135 cfm, 140 cfm, 145 cfm, 150 cfm, 155 cfm, 160 cfm, 165 cfm, etc.). In some cases, a blower can be controlled by a variable speed setting. For example, in some cases, speed settings can range from 5 cubic feet per minute (cfm) to 300 cfm (from 10 cfm to 200 cfm, from 10 cfm to 150 cfm, from 10 cfm to 100 cfm, from 10 cfm to 80 cfm, from 10 cfm to 60 cfm, from 10 cfm to 50 cfm, from 10 cfm to 40 cfm, or from 15 cfm to 40 cfm).

In some cases, the first and second air filtration systems are independently operable (i.e., can be controlled independently) (e.g., by separate controllers). For example, the blower (on/off, speed, etc.) for the first and second air filtration systems can be controlled with controls dedicated to each air filtration system. In some embodiments the controls can be found on an instrument control panel of the BSH. In some embodiments, the controls can be found on an associated processor (e.g., a computer). In some instances the first and second air filtration systems are physically and fluidically independent. In other words, the two filtration systems can be independently operated without causing negative effects on each other's fluidics system. When one of the filtration systems is turned on, it does not force air through the other filtration system. The first and second filtration systems may be self-contained and self-supporting independent entities. In these embodiments, the systems may be configured to avoid allowing air to be back flushed back into the hood if the main blower is off.

Processor.

In some embodiments, a subject BSH includes a processor. In some cases, a processor allows for user control of an air filtration system (e.g., the first (main) and/or second (redundant) air filtration systems of the BSH). In some embodiments, the processor is configured to receive an input (e.g., an input signal) from the flow cytometer and/or send a signal to the flow cytometer. Such input and output signals provide communication between the flow cytometer instrument and the BSH, e.g., to monitor specific error conditions and take appropriate, safe action if triggered. Various signals and inputs can be sent and/or received, including but not limited to: a signal reporting the status of a particular flow cytometric procedure (e.g., a cleaning procedure, a sorting procedure, etc.); a signal reporting the air flow rate (e.g., the air flow rate generated by at least one air filtration system of a BSH); a signal reporting the time remaining or time elapsed for a particular flow cytometric procedure; an error signal (e.g., an error signal generated in response to a clog in the flow path of the flow cytometer, an error signal generated by a sub-threshold air flow rate of an air filtration system); etc.

In some embodiments, an error signal is sent to the flow cytometer and/or received from the flow cytometer. In some cases, a processor of the BSH sends an error signal to the flow cytometer when the airflow (generated by at one or more of the air filtration systems) falls below a pre-determined threshold. In some cases, the error signal alerts the user to stop and/or pause sample flow through the flow path during a flow cytometric procedure. In some cases, the error signal instructs to the flow cytometer to automatically stop and/or pause sample flow through the flow path during a flow cytometric procedure. Error signals sent from the flow cytometer to the BSH can be useful, for example, in cases where a threshold level of air flow is required to safely remove aerosols during a flow cytometric procedure. In this way, when the cytometer sort head has an error (e.g., by a clog in the line, a faulty motor, a leak, etc.), the cytometer sends a signal to the BSH to increase airflow (e.g., when a clogged line is flushed out, increased amounts of particles can be generated that need to be evacuated).

Signals can be generated in a variety of different ways. In some cases, signals are generated by detectors/sensors that detect and report the status of particular parameters (e.g., the air flow rate being generated by one or more air filtration systems of a BSH, the flow rate of the flow path of a flow cytometer, etc.).

Instrument Control Panel.

In some embodiments, a BSH has an instrument control panel. An instrument control panel includes a processor to allow a user to control a feature of the BSH. In some embodiments, the instrument control panel is configured to allow a user to control the first (main) and/or second (redundant) air filtration systems of the BSH. In some cases, a BSH instrument control panel is configured to allow a user to control one or more steps of a decontamination procedure (described in more detail below). In some embodiments, the AMS evacuates the particle collection region and its operation can be controlled separately from the main system blower. In some embodiments, the instrument control panel will have controls (e.g., a dial, buttons, etc.) for actuating the blower of the AMS at two or more speed settings (e.g., LO for 15 cfm, and HI for 40 cfm).

Decontamination.

In some embodiments, a subject BSH is configured to perform a decontamination procedure. The term "decontamination procedure" is used herein to refer to a procedure that results in decontamination of the main enclosure (which, as described above, can be defined by surfaces of both the BSH and the flow cytometer instrument base, or can be defined solely by surfaces of the BSH). Decontamination can be performed manually, or various steps (or all steps) of decontamination can be performed in an automated manner (i.e., controlled by a processor). In some cases, the duration of at least one processor-controlled step of the decontamination procedure can be input into a processor by a user. Any convenient type of decontamination procedure can be performed. For example, decontamination procedures can include the use of ultraviolet (UV) light, decontaminating fluids, decontamination gases, etc.

In some embodiments, steps of a decontamination procedure include: (a) sealing the main enclosure to create a mini-environment comprising the flow cytometer; (b) introducing a decontamination gas into the mini-environment; and (c) removing the decontamination gas from the mini-environment.

Regarding step (a), as described above, the BSH and the flow cytometer instrument base can be attached in an air tight manner so that aerosols do not escape where surfaces of the BSH and instrument base meet. Instead aerosols are directed out of the main enclosure by the air filtration system(s) of the BSH. The step of sealing the main enclosure to create a mini-environment refers to the step of forming the air tight seals. For example, if rubber gaskets are used where the BSH and instrument base meet, sealing the main enclosure may encompass locking down clamps to assure a tight seal. As described above, in some embodiments, a subject BSH has a moveable panel (e.g., a sliding sash) that can be closed. In some such cases, the step of sealing the main enclosure to create a mini-environment includes closing the moveable panel in such a way that an air tight seal is formed (e.g., using locking clamps, simply sliding a sash into a locked position, using an automated locking and sealing mechanism, etc.).

Step (b), the step of introducing a decontamination gas into the mini-environment, refers to the controlled introduction of a known gas into the mini-environment. Any convenient decontamination gas can be used. In some embodiments, the decontamination gas is a sterilizer. The term "sterilizer" is used herein as it is defined by the United States Environmental Protection Agency (U.S. EPA): an antimicrobial pesticide that destroys or eliminates all forms of microbial life in the inanimate environment (including all forms of vegetative bacteria, bacterial spores, fungi, fungal spores, and viruses). Since sterilization includes eradication of all living microorganisms, such claims are intrinsically related to protection of human health. A list of substances considered to be sterilizers by the EPA (and are therefore suitable as decontamination gases when present in gaseous form) includes: (i) Hydrogen peroxide (e.g., 1%, 31%, 35%, 59%, 70%); (ii) hydrogen peroxide/enthaneperoxic acid (e.g., 1%/0.8%, 5.6%/0.3%, 22%/4.5%, 22%/15%, 24%/1.2%, 27%/2%, 27.5%/5.8%); (iii) hydrogen peroxide/enthaneperoxic acid/caprylic acid (e.g., 6.9%/4.4%/3.3%); (iv) sodium chlorite (e.g., 0.85%, 1.52%, 25%, 37%, 72.8%); (v) tetraacetylethylenediamine (e.g., 61.6%), 2,4-Dodecadienoic acid, 3,7,11-trimethyl-ethyl ester, (S-(E,E)) (e.g., 95%); (vi) 1-Decanaminium, N-decyl-N,N-dimethyl-chloride/Alkyl* dimethyl benzyl ammonium chloride *(50%014, 40% C12, 10% C16)/1-Octanaminium, N,Ndimethyl-N-octyl-chloride/1-Decanaminium, N,N-dimethyl-N-octyl-chloride (e.g., 0.06%/0.16%/0.06%/0.12%); (vii) ethylene oxide (e.g., 8.5%, 8.6%, 10%, 12%, 20%, 80%, 89.4%, 90%, 96%, 97%, 98.06%, 100%); (viii) sodium hypochlorite (e.g., 12.5%); (ix) Alkyl* dimethyl benzyl ammonium chloride *(50%014, 40% C12, 10% C16) (e.g., 0.3%); (x) sodium chlorite/sodium dichloroisocyanurate dehydrate (e.g., 20.8%/7%); (xi) silver (e.g., 0.03%, 0.78%, 17.5%); (xii) chloroxylenol (e.g., 4.51%); and (xiii) Tetrakis (hydroxymethyl)phosphonium sulphate (THPS)/Alkyl* dimethyl benzyl ammonium chloride *(50% C12, 30% C14, 17% C16, 3% C18) (e.g, 0.3%/0.5%). The preceding list of sterilizers was extracted from a table generated by the EPA in December 2011 entitled: "List A: Antimicrobial Products Registered with the EPA as Sterilizers".

In some embodiments, the decontamination gas is vaporized hydrogen peroxide (VHP). VHP can be produced from a solution of liquid hydrogen peroxide ($H_2O_2$) and water, in some cases using generators specifically designed for the purpose. Such generators initially dehumidify the ambient air, then produce VHP by passing aqueous hydrogen peroxide over a vaporizer, and circulate the vapor at a programmed concentration in the air. Various mixtures can be used and VHP can be used at a variety of concentrations (see list of sterilizers above). VHP is typically circulated at a concentration range from 140 parts per million (ppm) to 1400 ppm, which can depend on the infectious agent to be cleared. After the VHP has circulated in the enclosed space for a pre-defined period of time, it can be re-collected, where it can be broken down into water and oxygen by a catalytic converter, until concentrations of VHP fall to safe levels (typically <1 ppm). Alternatively, the VHP can be vented to the outside air, in cases where recapturing of the VHP is not desired and/or needed.

In some embodiments, the decontamination gas is chlorine dioxide gas (i.e., gaseous chlorine dioxide). For information regarding the use of chlorine dioxide gas, refer to U.S. patent application US20080286147, which is hereby incorporated by reference in its entirety.

In some embodiments, a gas source is used. A suitable gas source can be any gas-containing container in fluid communication with the mini-environment. In some cases, the gas source is pressurized so that gas will flow from the gas source to the mini-environment. In some cases, the gas source includes an engine (e.g., the gas source is motorized) that can generate air flow from the gas source to the mini-environment. In some cases, the gas source can produce particular formulations of gas mixtures prior to, or during, introduction of the mixture into the mini-environment. In some cases, the gas source includes a humidifier. In some cases, the gas source is portable (e.g., removable). In some cases, the gas source can be stored in the flow cytometer instrument base. In some embodiments, the introduction of decontamination gas into the mini-environment includes a step of actuating a gas source (e.g., opening a valve to allow fluid communication between the gas source and the mini-environment, actuating a motor or utilizing pressure to induced gas flow, etc.).

The decontamination gas is allowed to remain in the mini-environment for a period of time sufficient to provide the desired level of decontamination, and such periods of time (exposure times) will be depend on many factors including temperature, air flow, volume of the mini-environment, formulation and concentration of the gas, suspected level of contamination, etc.

Step (C), the step of removing the decontamination gas from the mini-environment can be performed by any convenient method. For example, in some cases, the decontamination gas can be blown out of the mini-environment using the blower of the first (main) air filtration system of the BSH. In some such cases, an air filter is used and in some such cases, an air filter is not used. In some embodiments, the decontamination gas can be re-collected (e.g., for re-use, for discarding, for hazardous waste pick-up, for catalytic conversion to a safer variety of gas, etc.), or neutralized.

In some embodiments, a decontamination procedure includes a step of modulating flow of the decontamination gas (e.g., circulating the decontamination gas) within the mini-environment, thus increasing exposure of surfaces to the decontamination gas. In some embodiments, modulating flow includes actuating an air filtration system (e.g., actuating the blower of the main air filtration system and/or the blower of the AMS). In some cases, modulating flow includes alternatively, and repeatedly actuating the blower of the main air filtration system and actuating the blower of the AMS (e.g., "pulsing" the blowers of the air filtration systems). In some cases, the evacuation ports of the air filtration systems are closed and the decontamination gas is re-circulated during the step of modulating flow. In some cases, the evacuation ports of the air filtration systems are open during the step of modulating flow, and decontamination gas is continually added to the mini-environment, thus creating a flow of decontamination gas from the gas source to the evacuation port.

Flow Cytometer Instrument Base

In some embodiments, the present disclosure provides a "flow cytometer instrument base", also referred to herein simply as an "instrument base". A subject flow cytometer instrument base supports the weight of a flow cytometer and provides a surface with which a flow cytometer can associate. For example, a subject instrument base can provide an upward facing surface upon which a flow cytometer can rest. The flow cytometer can be attached to the instrument base, or can simply rest upon the instrument base, being held in place by the force of gravity. Alternatively, a subject instrument base can provide a weight-bearing, non-upward facing surface to which a flow cytometer can attach. In cases where the flow cytometer attaches to the instrument base, any convenient type of attachment (e.g., bolts, clamps, pegs, latches, screws, magnets, adhesives, and the like) can be used. Thus, in some cases, the instrument base is configured to attach to a flow cytometer, and/or the flow cytometer is configured to attach to the instrument base (see "enclosure" above). In yet other instances, a flow cytometer may be integrated, at least partially, with an instrument base, e.g., where certain fluidics and/or electronics of the flow cytometer are integrated into one portion of the base, and the sort head/optics are integrated into another portion of the base. In these instances, the integrated flow cytometer and cytometer instrument base may include: a cytometer base which includes an cytometer electronics component, e.g., drawer that houses the laser(s) and cytometer processing functionalities, and a fluidics component, e.g., drawer, that houses the supporting fluids. On top of the base may be the cytometer sort head, sort housing or sort area, which house the optics, sort chamber, and sample line.

The exact dimensions and shape of the instrument base will vary based on the dimensions of the flow cytometer to be enclosed, and/or based on the BSH to which the instrument may attach. Generally, a suitable instrument base can be any shape and/or size as long as the instrument base can attach to a BSH such that the main enclosure is large enough to contain a flow cytometer. An instrument base can support the weight of a flow cytometer and a BSH.

In some embodiments, the height of the instrument base can be in a range of from 1 foot (ft) to 5 ft (e.g., from 2 ft to 4 ft, from 2.5 ft to 3.5 ft, from 3 ft to 3.5 ft, 2 ft, 2.5 ft, 3 ft, 3.5 ft, 4 ft, 4.5 ft, or 5 ft).

In some cases, the width of the instrument base can be in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the instrument base is designed to support a flow cytometer, the width of the instrument base is equal to or greater than the width of the flow cytometer. In some cases, the width of the instrument base can be in a range of from 100.05% to 250% the width of the flow cytometer to which the instrument is to be associated (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some cases, the depth of the instrument base can be in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the instrument base is designed to support a flow cytometer, the depth of the instrument base is equal to or greater than the depth of the flow cytometer. In some cases, the depth of the instrument base can be in a range of from 100.05% to 250% the depth of the flow cytometer to which the instrument is to be associated (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 122.5%, from 100.05% to 120%, from 100.05% to 115%, from 100.05% to 110%, from 100.05% to 107.5%, from 100.05% to 105%, or from 100.05% to 102.5%).

Fluid Source.

In some embodiments, a flow cytometer instrument base includes a fluid source (e.g., a gas or liquid source). In some cases, the fluid source may be sealed to maintain sterility of the contained fluid. For example, the fluid source may be closed to the surrounding environment to prevent undesired contact between the fluid and the surrounding environment. Although the fluid source may be sealed from the surrounding environment, the fluid source may include one or more ports, such as one or more inlets and/or outlets. The one or more ports may be configured to permit access to the interior of the fluid source when desired. For example, the fluid source may include an inlet configured to allow a fluid, such as a sample fluid, reagent, wash buffer etc. to be added to the fluid source. In some cases, the fluid source includes an outlet configured to allow fluid from the fluid source to be removed from the fluid source. The ports may be self-sealing ports, such that fluid can be added or removed from the fluid source, for example using a syringe, and then the port seals itself to prevent contact between the fluid in the fluid source and the surrounding environment.

In some instances, the fluid source includes a fluid outlet. The fluid outlet may be configured to carry the fluid as the fluid flows out of the fluid source. The fluid outlet may be in fluid communication (fluidically coupled) with a flow cytometer. The fluid outlet may be in fluid communication with a mini-environment, where the mini-environment is created by sealing the main enclosure of a subject flow cytometer system (e.g., where BSH and instrument base are attached). In some cases, the fluid source is directly connected to the component with which it is in fluidic communication. In other embodiments, the fluid source is connected to the component with which it is in fluidic communication via a conduit (e.g., a hose, tubing, flexible ducting, etc.). In some cases, the fluid source further includes a clamp. The clamp may be configured to block the flow of fluid from the fluid source. For instance, the clamp may be positioned around the conduit. When configured in a closed position, the clamp substantially blocks the conduit, for example by pinching the conduit to occlude the inner lumen, and thus preventing fluid from flowing through the conduit. When configured in an open position, the clamp does not block the flow of fluid through the conduit.

In some embodiments, the fluid source is made of a polymer, such as, but not limited to, polyvinyl chloride (PVC), ethyl vinyl acetate (EVA), polyethylene, polypropylene, combinations thereof, and the like.

In certain embodiments, the fluid source includes one chamber that includes the fluid. In other cases, the fluid source includes two or more chambers. The two or more chambers may contain the same or different fluids. For example, a first fluid source chamber may contain a first fluid and a second fluid source chamber may contain a second fluid. A fluid source comprising two or more chambers may facilitate the mixing of fluids, where the first sample fluid is contained in the first fluid source chamber and the second sample fluid is contained in the second fluid source chamber. The two or more chambers may be configured to be in fluid communication with a single conduit or with two or more conduits, as desired. For instance, the two or more chambers may be in fluid communication with one conduit. The lumens of the two or more chambers may be joined together at a Y-connector, a valve (e.g., a pinch valve), or the like.

In some cases, the instrument base has a door or removable panel to allow user access to a fluid source. In some cases, the fluid source is removable (i.e., the fluid source can be removed from the instrument base). In some embodiments, the instrument base has a support for the fluid source. In some embodiments, the support is extendible (e.g., at least partially extendible) away from the body of the instrument base to allow user access to the fluid source. In some cases, the extendible support for the fluid source is a drawer.

As described above, a suitable flow cytometer instrument base can attach to a biosafety hood (BSH). In some embodiments, a flow cytometer has non-aerosol generating components that are not part of the sample flow path and are not contained by the enclosure of the BSH. For example, components such as spectral filters, lasers, detector arrays, etc. can be housed outside of the main enclosure and/or outside of the BSH. For example, in some embodiments, a flow cytometer instrument base contains non-aerosol generating components (e.g., spectral filters, lasers, detector arrays, and the like) of an associated flow cytometer (FIG. 7C).

An example of a sample manipulation chamber 30 (having an access hole 31, an influx opening 32, and an efflux opening 33) is shown in FIG. 1. FIG. 1A depicts the sample manipulation chamber 30 alone, while FIG. 1B depicts a sample manipulation chamber 30 attached to components 41 and 42 of a flow cytometer. For example, FIG. 1B depicts a mobile arm 41 (e.g., a mobile arm of a flow cytometer) that penetrates the access hole 31 of the sample manipulation chamber 30. Notice that without a subject sealing cartridge, the access hole 31 of the sample manipulation chamber 30 is unsealed and allows airflow into and/or out of the sample manipulation chamber 30. FIG. 1C depicts simulated airflow streamlines 38 for a sample manipulation chamber 30 where air flows in through an influx opening 32 and out through an efflux opening 33. The streamlines depicting flow from the influx opening are hidden so that streamlines 38 caused by airflow through an access hole 31 are visible. The chamber on the left has a sealed access hole 31 while the chamber on the right has an unsealed access hole 31. FIG. 1D depicts the same simulated airflow streamlines 38 as depicted in FIG. 1C, however the streamlines flowing from the influx opening are not hidden in order to visualized the overall disturbance in airflow caused having an unsealed access hole 31.

An example of one embodiment of a sample manipulation chamber 30 attached to a sealing cartridge 20 according to the present disclosure is shown in the schematic illustrations (top view, side view, and angled view) presented in FIG. 2. The sealing cartridge 20 depicted includes a winder 28 at one end (the same end as the influx opening 32 of the sample manipulation chamber 30), and includes a slider tape 1 that is enclosed within the sealing cartridge 20. The sealing cartridge 20 is attached to the sample manipulation chamber 30 so that the access hole (not seen) of the sample manipulation chamber 30 is adjustably sealed by the sealing cartridge 20. Also depicted is an access hole 4 of the slider tape 1, which allows for penetration of the sample manipulation chamber 30 where the access hole 4 of the slider tape 1 aligns (i.e., overlaps) with the access hole (not seen) of the sample manipulation chamber 30.

An example of one embodiment of a slider tape 1 according to the present disclosure is shown in FIG. 3. The depicted slider tape 1 has an access hole 4, can reversibly wind upon itself 3, and has a rigid region 2 that cannot reversibly wind upon itself, where the rigid region includes one end of the slider tape 1 and surrounds the access hole 4.

An embodiment of a sealing cartridge 20 (having a slider tape 1) according to the present disclosure is shown in FIG. 4. The depicted sealing cartridge 20 has a back plate 21 with an access hole 22 and a front plate 26 with an access hole 27. The back plate 21 and front plate 26 attach to one another to enclose the slider tape 1, and the slider tape 1 can slide within the track of the sealing cartridge 20 to allow for an adjustable seal (e.g., to adjustably seal a sample manipulation chamber). The depicted front plate 26 has a winder 28 on one end, but not on the opposite end. As noted above, in some cases, a sealing cartridge has two winders, which can be located at opposite ends of the sealing cartridge. The depicted slider tape 1 can wind and un-wind upon itself (i.e., reversibly wind) upon entering and exiting (e.g., via sliding) the winder 28 of the sealing cartridge 20. Also depicted is an access hole 4 of the slider tape 1, which allows for penetration of the sealing cartridge 20 (and therefore penetration of a sample manipulation chamber (not seen)) where the access hole 4 of the slider tape 1 aligns (i.e., overlaps) with the access holes 22 and 27 of the back plate 21 and the front plate 26.

Figure 6A:
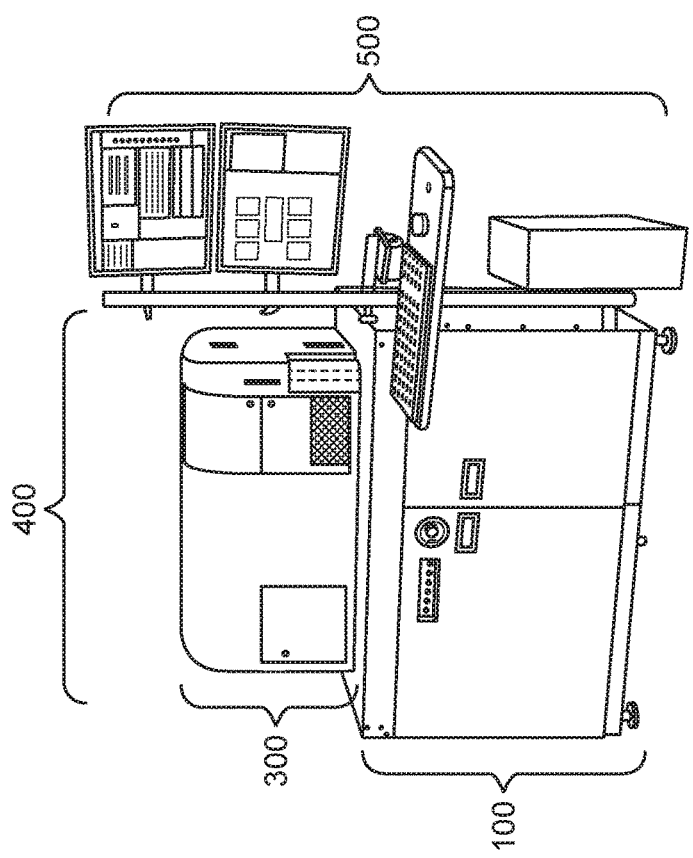

An example of an embodiment of a flow cytometry system according to the present disclosure is shown in the schematic illustrations and pictures presented in FIG. 5 and FIG. 6. A flow cytometry system 400 can include any combination of three main components: a flow cytometer instrument base 100, a biosafety hood (BSH) 200, and a flow cytometer 300. FIG. 5 shows a flow cytometer system 400 that includes the three components: a flow cytometer instrument base 100, a BSH 200, and a flow cytometer 300, where the flow cytometer 300 has a sample manipulation chamber 30. FIG. 6 shows a flow cytometer system 400 that includes two of the three components: a flow cytometer instrument base 100, and a flow cytometer 300, where the flow cytometer 300 has a sample manipulation chamber 30. The access hole 31 of the sample manipulation chamber 30 is also visible. A BSH can be added to the flow cytometer system of FIG. 6 at any time. Thus, the instrument base 100 of FIG. 6 can be configured to attach to a subject BSH. The flow cytometer systems of FIGS. 5A and 6A also include a processor, which in the depicted embodiment is part of an entire computer workstation 500.

FIG. 7 depicts various components and various embodiments of a flow cytometer system. FIG. 7A depicts a step of introducing a sample into a sample loading region 310 of a flow cytometer 300 of a subject flow cytometer system that includes a flow cytometer instrument base 100, and biosafety hood (BSH) 200. Depicted is a user inserting a sample into the sample loading region 310.

Figure 1B:
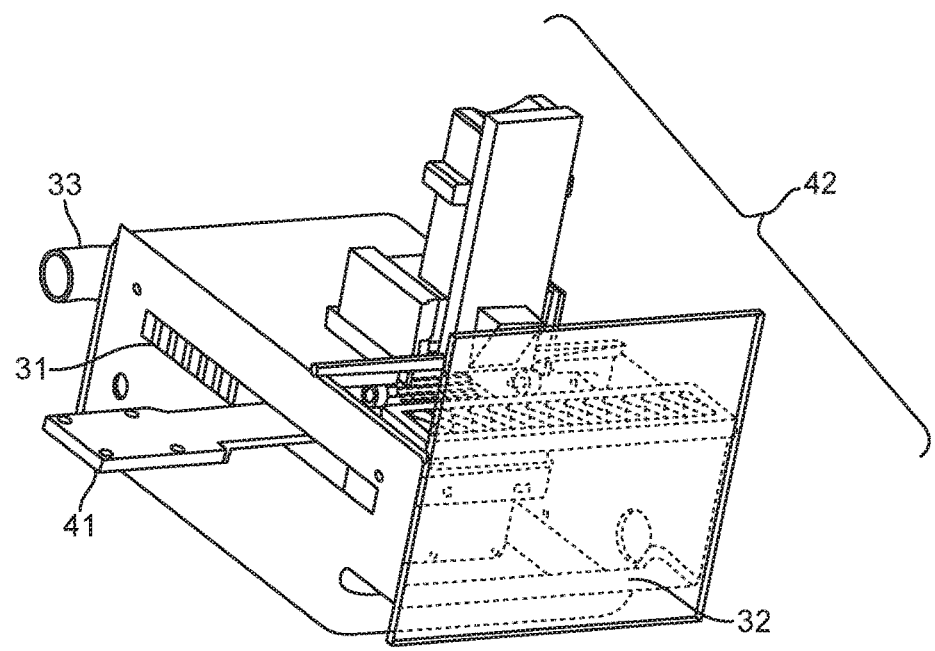
Figure 1C:
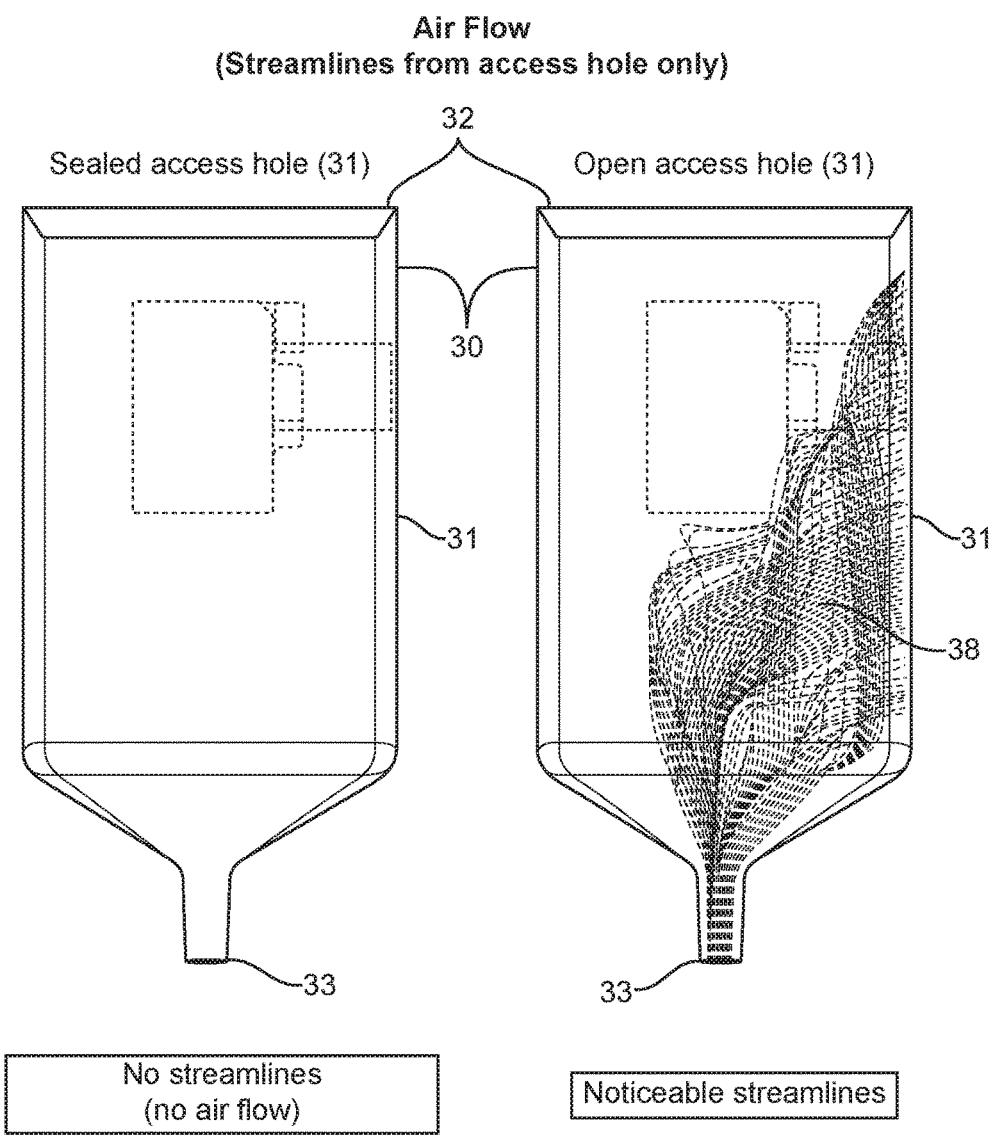
Figure 1D:
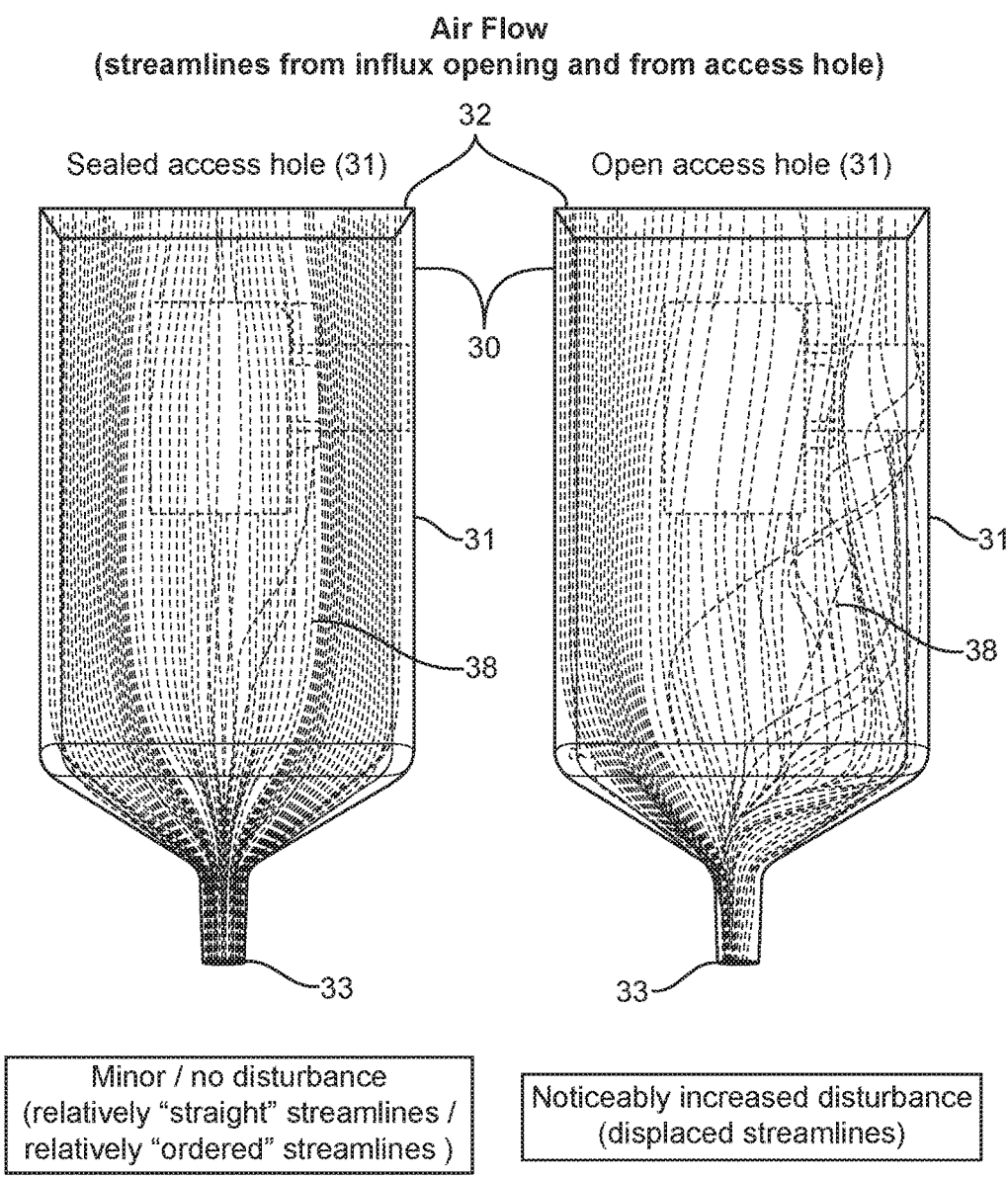

FIG. 7B depicts an operator (i.e., a user) manipulating a sample within a particle collection region 330 of a flow cytometer 300, where the flow cytometer system includes a BSH. The particle collection region includes a sample manipulation chamber 30, which encloses the particle collection region. A sash on the front of the BSH is pulled down so that only a small space exists where the user is extending their arms into the main enclosure. In the depicted embodiment, the sample manipulation chamber 30 of the particle collection region 330 has been opened to allow the user access, and the user is accessing the sample manipulation chamber 30 through the influx opening 32. While performing a cytometric procedure, the particle collection region 330 can be closed to in order to trap aerosols generated during the procedure. Thus, the particle collection region 330 depicted can be an enclosed, air-tight sample chamber (e.g., surrounded by a sample manipulation chamber 30) with the exceptions that (i) there can be a filter on one side to allow clean air into the sample chamber through the influx opening 32; (ii) there can be an efflux opening on one side (e.g., the back) that can fluidically couple to an AMS, e.g., the opening can be connected to a conduit (e.g., a hose, flexible tubing, flexible ducting, etc.) that can connect to an AMS (FIG. 8), which generates air flow (e.g., in through the influx opening 32, through the particle collection region within the sample manipulation chamber 30, and out through the efflux opening); (iii) there can be an access hole that is adjustably sealed by a subject sealing cartridge, which is configured to allow a mobile arm to adjustably penetrate the sample manipulation chamber; and (iv) there can be an opening to allow the flow path of the flow cytometer to enter the sample manipulation chamber (e.g., on top of the sample manipulation chamber 30, as depicted in FIG. 1B). An optional AMS can be included in the BSH such that aerosols generated in the particle collection region 330 are removed by the air flow generated by the blower of the AMS.

FIG. 7C depicts a flow cytometer instrument base 100 that houses detector arrays of an associated flow cytometer. In the depicted embodiment, the flow cytometer has non-aerosol generating components (octagon detector arrays), which are not part of the sample flow path, do not generate aerosols, and are not contained by the enclosure of the BSH. Instead, the components are contained in the flow cytometer instrument base 100. As discussed above, the phrase "the flow cytometer is present in an enclosure defined by the BSH and the flow cytometer instrument base" does not mean that all components of the flow cytometer are necessarily contained within the main enclosure. Instead, such a phrase means that at least the flow path (i.e., the potential aerosol generating components: the sample loading region, the particle interrogation region, and the particle collection region) of the flow cytometer is present in the main enclosure. In the depicted embodiment, a user is manipulating one of the detector arrays of the flow cytometer.

Figure 7D:
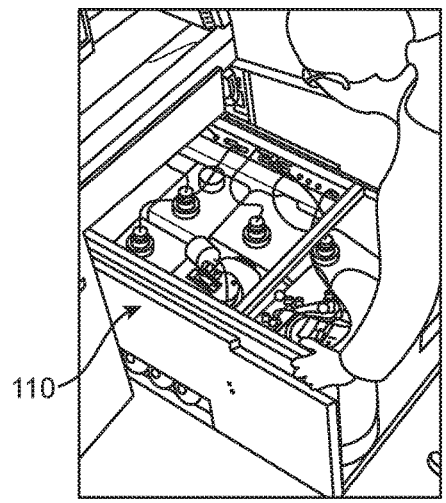

FIG. 7D depicts a flow cytometer instrument base 100 having multiple removable fluid sources in a drawer that is extendible from the base. In the depicted embodiment, a user has extended the base and has gained access to the removable fluid sources. Hoses can be seen that fluidically couple the fluid sources to other components of the flow cytometer system.

FIG. 8 depicts a cutaway schematic of one embodiment of a biosafety hood (BSH) having an aerosol management system (AMS) 240 that is fluidically coupled via conduit 220 to the efflux opening 33 of the sample manipulation chamber 30 of the particle collection region 320 of a flow cytometer 300. The sample manipulation chamber 30 of the particle collection region 320 has an air filter 310 covering the influx opening 32 of the sample manipulation chamber 30, which faces toward the front of the flow cytometer 300. The BSH depicted has an upper region that houses first and a second air filtration systems 250. When the AMS 240 is operating (i.e., when the AMS is actuated), air flows from the front of the flow cytometer, through a forward-facing air filter 310, which covers the influx opening 32 of the sample manipulation chamber 30, through the particle collection region 320, toward the back of the flow cytometer, out of the efflux opening 33 of the sample manipulation chamber 30, into the conduit 220, and toward the blower of the AMS 240. A subject sealing cartridge can be attached to the sample manipulation chamber 30 to adjustably seal the access hole 31 of the sample manipulation chamber 30. The sealing cartridge can be penetrated by a mobile arm configured to manipulate samples within the sample manipulation chamber 30.

FIG. 9 depicts cutaway schematics (zoomed in compared to FIG. 8) of one embodiment of a flow cytometer system where the efflux opening 33 of the sample manipulation chamber 30 of the particle collection region 320 of a flow cytometer is fluidically coupled via conduit 220 to an aerosol management system (AMS) of a biosafety hood (BSH). The sample manipulation chamber 30 of the particle collection region 320 has an air filter 310 covering the influx opening 32 of the sample manipulation chamber 30. When the associated AMS (not depicted) is operating (i.e., when the AMS is actuated), gas (e.g., ambient air, decontamination gas, etc.), in some cases containing aerosols, flows (depicted with arrows) from the front of the flow cytometer, through a forward-facing air filter 310 covering the influx opening 32 of the sample manipulation chamber 30, through the particle collection region 320, toward the back of the flow cytometer, out of the efflux opening 33 of the sample manipulation chamber 30, into the conduit 220, and toward the AMS. A subject sealing cartridge can be attached to the sample manipulation chamber 30 to adjustably seal the access hole 31 of the sample manipulation chamber 30. The sealing cartridge can be penetrated by a mobile arm configured to manipulate samples within the sample manipulation chamber 30.

Methods

Aspects of the present disclosure include methods of using a subject flow cytometer system. Provided are methods of performing a flow cytometric procedure. The methods generally include introducing a sample into a subject flow cytometer system (where the flow cytometer includes a mobile arm that penetrates into a sample manipulation chamber); and flow cytometrically analyzing particles of the sample. In some cases, the methods include actuating at least one of the first (main) and second (AMS) air filtration systems of a subject flow cytometer system. For example, in performing a flow cytometric analysis, a user can actuate a first and/or second air filtration system to remove aerosols generated during the analysis (i.e., during operation of the flow cytometer).

The term "flow cytometrically analyzing" is used herein to mean the analysis of particles using a flow cytometer. As described above, analysis can include recording data associated with various measured parameters (e.g., light scatter, fluorescence, etc.) of particles in a sample. In some cases, "flow cytometrically analyzing" includes sorting particles based on the measured parameters. In some cases, "flow cytometrically analyzing" includes manipulating samples within the sample manipulation chamber using a mobile arm that penetrates through a subject sealing cartridge and into the sample manipulation chamber. In some cases, the mobile arm is adjusted (e.g., moved relative to the sample manipulation chamber) while samples are not concurrently being analyzed. For example, in some cases, the mobile arm can be adjusted before a given sample is analyzed. In some cases, the mobile arm is adjusted (e.g., moved relative to the sample manipulation chamber) while samples are concurrently being analyzed (i.e., during sample analysis).

A "sample" as used herein refers to any particle-containing liquid sample suitable for flow through the flow path of a flow cytometer. Dangerous aerosols can be generated during a flow ctyometric procedure even if the contained particles are not cells. For example, in some cases, a sample contains microparticles, which may be considered biohazardous under certain circumstances (e.g., if the microparticles are labeled with hazardous labels such as toxins or radioactive elements). In some cases, a sample contains viruses. Particles contained in the sample are generally separated from one another to allow for flow through the flow path of a flow cytometer.

A "biological sample" encompasses a variety of sample types obtained from an organism (or obtained in vitro, e.g., via cell culture) that is substantially in liquid form. Particles contained in the biological sample are generally separated from one another to allow for flow through the flow path of a flow cytometer. The definition encompasses blood, blood-derived samples, and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, enrichment for certain components, or labeling (e.g., labeling with a label). The term "biological sample" encompasses a clinical sample, and also includes cells in culture, cell supernatants, cell lysates, serum, plasma, cerebrospinal fluid, urine, saliva, biological fluid, and tissue samples. Any convenient method for preparing a biological sample (e.g., a biopsy) for use in a flow cytometric assay can be used.

Also provided are methods of decontaminating a flow cytometer system. Such methods are described in detail above and can include: (a) sealing the main enclosure to create a mini-environment comprising the flow cytometer; (b) introducing a decontamination gas into the mini-environment; and (c) removing the decontamination gas from the mini-environment. Decontamination can be performed manually, or various steps (or all steps) of decontamination can be performed in an automated manner (i.e., controlled by a processor). In some embodiments, the sash of a BSH is closed by the user and a decontamination button on an instrument panel of the BSH is then depressed to initiate introduction of the decontamination gas into the mini-environment. In some cases, once depressed, an automated decontamination procedure will proceed and the user can reopen the sash once the procedure is finished. In some embodiments, a mobile arm that penetrates a subject sealing cartridge into the sample manipulation chamber can be adjusted before and/or after a decontamination procedure. In some embodiments, such a mobile arm can be adjusted during a decontamination procedure.

The step of sealing the main enclosure to create a mini-environment refers to a step of forming the air tight seals. For example, if rubber gaskets are used where the BSH and instrument base meet, sealing the main enclosure may encompass locking down clamps to assure a tight seal. As described above, in some embodiments, a subject BSH has a moveable panel (e.g., a sliding sash) that can be closed. In some such cases, the step of sealing the main enclosure to create a mini-environment includes closing the moveable panel in such a way that an air tight seal is formed (e.g., using locking clamps, simply sliding a sash into a locked position, using an automated locking and sealing mechanism, etc.).

Step (b), the step of introducing a decontamination gas into the mini-environment, refers to the controlled introduction of a known gas (exemplary decontamination gases are provided above) into the mini-environment. The decontamination gas is allowed to remain in the mini-environment for a period of time sufficient to provide the desired level of decontamination, and such periods of time (exposure times) will be depend on many factors including temperature, air flow, volume of the mini-environment, formulation and concentration of the gas, suspected level of contamination, etc. In some cases, the duration of at least one processor-controlled step of the decontamination procedure can be input into a processor by a user. For example, in some embodiments, the user chooses the amount of time (e.g., using an instrument panel of the BSH, using an associated processor such as a computer, etc.) that the decontamination gas will remain in the mini-environment prior to being removed (e.g., via actuation of the main blower and/or AMS blower).

In some embodiments, a decontamination procedure includes a step of modulating flow of the decontamination gas (e.g., circulating the decontamination gas) within the mini-environment, thus increasing exposure of surfaces to the decontamination gas. In some embodiments, modulating flow includes actuating an air filtration system (e.g., actuating the blower of the main air filtration system and/or the blower of the AMS). In some cases, modulating flow includes alternatively, and repeatedly actuating the blower of the main air filtration system and actuating the blower of the AMS (e.g., "pulsing" the blowers of the air filtration systems). In some embodiments, modulating flow of the decontamination gas is automated such that the user does not control the modulating step. In some embodiments, the user has the option to include or not include (e.g., turn "on" or "off" the feature) the step of modulating flow. In some cases, the user can control various parameters of the modulating step (e.g., the flow rate(s) of one or more of the air filtration systems, the timing of blower "pulses", the strength of blower "pulses", the duration of blower "pulses", etc.). In some embodiments, various alternative configurations of the above parameters are pre-programmed into a processor (e.g., a processor of the BSH, a processor of an associated computer, etc.) and a user can choose which configuration to select.

In some embodiments, the evacuation ports of the air filtration systems are closed and the decontamination gas is re-circulated during the step of modulating flow. In some cases, the evacuation ports of the air filtration systems are open during the step of modulating flow, and decontamination gas is continually added to the mini-environment, thus creating a flow of decontamination gas from the gas source to the evacuation port.

Utility

Embodiments of the subject components, systems, and methods find use in a variety of different applications where it is desirable to manipulate samples within a sample manipulation chamber while maintaining a seal around the access hole of the chamber (e.g., when it is desirable to remove aerosols from the air surrounding a flow cytometer while maintaining the ability to manipulate samples with a mobile arm that penetrates the sample manipulation chamber). Embodiments of the subject components, systems, and methods find use in the safe use of a flow cytometer for the analysis/evaluation of hazardous substances, including hazardous chemicals and/or hazardous particles (e.g., toxins, infectious disease agents, infected cells, etc.), which can become airborne in the form of aerosols while performing a flow cytometric procedure. The flow cytometer systems of the present disclosure provide aerosol containment for external personal protection and internal protection of the flow cytometer instrument. Airborne hazardous substances generated during flow cytometer operation are in the form of small particles. These particles are directed away from operators by an air flow system, in some cases to collection filters (e.g., High Efficiency Particulate Air (HEPA) filters). The hazardous airborne substances are also managed away from the instrument itself where they could contaminate surfaces, thereby exposing operators who may come in contact with work surfaces.

A subject sealing cartridge allows for sample manipulation within the sample manipulation chamber while maintaining closure of the access hole of the sample manipulation chamber. This in turn increases safety by maintaining a sealed environment surrounding the particle collection region, and also maintains a more consistent and streamlined fluid flow (e.g., air flow) throughout the particle collection region during operation (which decreases cross-sample contamination)(see e.g., FIG. 1C-D).

For example, a flow cytometric system of the disclosure can provide a safe system with which to perform flow cytometric analysis of clinical and/or research samples. For example, in some cases, a clinical sample (e.g., blood, serum, urine, lymph, ascites, and the like) may be contaminated with harmful organisms (e.g., bacteria, fungi, protists, etc.) and/or may contain human cells infected with virus (e.g., human immunodeficiency virus (HIV), ebola virus, hanta virus, herpes simplex virus, etc.), and the subject flow cytometric systems provide an environment for performing powerful experimental procedures (e.g., cell analysis and/or sorting) under safe conditions for the user. The subject sealing cartridge allows for simplified sample manipulation before, during, and/or after sample analysis, while maintaining a safe environment.

Thus, the components of the disclosure provide for sample manipulation within the sample manipulation chamber (e.g., during sample analysis), while allowing for the removal of hazardous aerosols from areas of potential human exposure, to a filtration system where they are removed (e.g., trapped) and rendered harmless. Further, components of the disclosure provide for removal of hazardous aerosols from areas where they may collect on surfaces that would then come into human contact via operation of the instrument. Components of the disclosure also provide an environment for flow cytometric analysis with a greatly reduced risk of cross-contamination of samples. For example, when particles (e.g., cells) are sorted and collected, it is important that collected samples are not contaminated with aerosols (e.g., cells) from a previous use. It is also important that the access hole of the sample manipulation chamber is sealed to maintain a more streamlined and consistent fluid flow (e.g., air flow) throughout the particle collection region, thus reducing cross-sample contamination (see e.g., FIG. 1C-D).

The components of the disclosure (e.g., a sample manipulation chamber with an attached sealing cartridge, a sealing cartridge, and a slider tape) allow for a reduced footprint of a subject sealing cartridge. For example, a slider tape with a reversibly windable end and an associated winder dramatically reduces the amount of space required to allow for motion of the slider tape along an associated track. In some cases, a subject sealing cartridge is attached to (and adjustably seals) a sample manipulation chamber that is associated with a larger instrument (e.g., a flow cytometer). In some such cases, the dimensions of the larger instrument places space constraints on the dimensions of the sample manipulation chamber and/or the sealing cartridge. The provided slider tape and sealing cartridge have a small footprint that can alleviate space constraints.

The disclosed sample manipulation chamber, the sealing cartridge, and the sealing tape are not necessarily limited to the context of a flow cytometer. Any situation for which it is desired to have an adjustable seal so that a mobile arm can penetrate into a sealed environment is envisioned.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A flow cytometer comprising:
   (a) a sample manipulation chamber comprising an access hole;
   (b) a sealing cartridge adjustably sealing the access hole of the sample manipulation chamber, wherein the sealing cartridge comprises:
      (i) a slider tape comprising an access hole, and
      (ii) a first winder at one end of the slider tape, configured to reversibly wind the slider tape; and
   (c) a mobile arm penetrating the access holes of the slider tape and the sample manipulation chamber.

2. The flow cytometer according to claim 1, wherein the mobile arm is configured to manipulate samples in the sample manipulation chamber.

3. The flow cytometer according to claim 1, wherein the flow cytometer comprises a sample collection vessel within the sample manipulation chamber.

4. The flow cytometer according to claim 3, wherein the mobile arm is configured to manipulate the sample collection vessel.

5. The flow cytometer according to claim 1, wherein the sample manipulation chamber comprises an influx opening and an efflux opening, configured so that fluid flows into the sample manipulation chamber through the influx opening and out of the sample manipulation chamber through the efflux opening.

6. The flow cytometer according to claim 1, further comprising an air filtration system fluidically coupled with the sample manipulation chamber.

7. The flow cytometer according to claim 1, wherein the flow cytometer comprises an excitation light source.

8. The flow cytometer according to claim 1, wherein the flow cytometer comprises a detector.

9. The flow cytometer according to claim 1, wherein the flow cytometer comprises a deflection plate.

10. The flow cytometer according to claim 1, wherein the sealing cartridge comprises a first winder at one end of the slider tape and a second winder at the other end of the slider tape, wherein the first and second winders are each configured to reversibly wind the slider tape.

11. The flow cytometer according to claim 1, wherein the sealing cartridge comprises a front plate and a back plate attached to one another and enclosing the slider tape.

12. A method of performing a flow cytometric procedure, the method comprising:
   (a) introducing a sample into a flow cytometer comprising:
      (i) a sample manipulation chamber comprising and an access hole;
      (ii) a sealing cartridge adjustably sealing the access hole of the sample manipulation chamber, wherein the sealing cartridge comprises:
         (a) a slider tape comprising an access hole, and
         (b) a winder at one end of the slider tape, configured to reversibly wind the slider tape; and
      (iii) a mobile arm penetrating the access holes of the slider tape and the sample manipulation chamber; and
   (b) manipulating with the mobile arm a sample collection vessel within the sample manipulation chamber.

13. The method according to claim 12, wherein the flow cytometer comprises an air filtration system fluidically coupled with the sample manipulation chamber.

14. The method according to claim 13, further comprising actuating the air filtration system.

15. The method according to claim 12, further comprising flow cytometrically analyzing particles of the sample.

16. The method according to claim 15, wherein flow cytometrically analyzing comprises sorting particles of the sample into one or more sample collection vessels.

17. The method according to claim 16, wherein sorting particles of the sample includes the manipulating of step (b).

18. A sample manipulation system comprising:
   (i) a sample manipulation chamber comprising an access hole; and
   (ii) a sealing cartridge adjustably sealing the access hole of the sample manipulation chamber, wherein the sealing cartridge comprises:
      (a) a slider tape comprising an access hole, and
      (b) a first winder at one end of the slider tape, configured to reversibly wind the slider tape.

19. The sample manipulation system according to claim 18, wherein the sample manipulation chamber comprises an influx opening and an efflux opening, configured so that fluid flows into the sample manipulation chamber through the influx opening and out of the sample manipulation chamber through the efflux opening.

20. The sample manipulation system according to claim 18, wherein the sealing cartridge comprises a first winder at one end of the slider tape and a second winder at the other end of the slider tape, wherein the first and second winders are each configured to reversibly wind the slider tape.

* * * * *